(12) United States Patent
Lee et al.

(10) Patent No.: US 9,844,357 B2
(45) Date of Patent: Dec. 19, 2017

(54) RADIOGRAPHIC IMAGING APPARATUS AND METHOD OF CONTROLLING THE SAME

(71) Applicant: SAMSUNG ELECTRONICS CO., LTD., Suwon-si (KR)

(72) Inventors: Chang Lae Lee, Suwon-si (KR); Rifu Toshihiro, Suwon-si (KR); Ji Young Jung, Bucheon-si (KR); Jong Hyon Yi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 109 days.

(21) Appl. No.: 14/695,170

(22) Filed: Apr. 24, 2015

(65) Prior Publication Data

US 2016/0113615 A1    Apr. 28, 2016

(30) Foreign Application Priority Data

Oct. 28, 2014  (KR) .......................... 10-2014-0147465

(51) Int. Cl.
*A61B 6/04*  (2006.01)
*A61B 6/00*  (2006.01)
(Continued)

(52) U.S. Cl.
CPC .............. *A61B 6/542* (2013.01); *A61B 6/032* (2013.01); *A61B 6/0407* (2013.01);
(Continued)

(58) Field of Classification Search
CPC ....... A61B 6/032; A61B 69/542; A61B 6/545; A61B 6/405; A61B 6/0407
See application file for complete search history.

(56) References Cited

U.S. PATENT DOCUMENTS 5,805,659 A    9/1998  Tam
6,023,494 A *  2/2000  Senzig .................. A61B 6/032
                                                378/15
(Continued)

FOREIGN PATENT DOCUMENTS

JP           716152 U    3/1995
JP      2008116388 A     5/2008
(Continued)

OTHER PUBLICATIONS

Kalra et al., "Strategies for CT Radiation Dose Optimization," Radiology 2004, vol. 230, p. 619, 628; Retreived from internet [Sep. 12, 2016]; Retrieved from URL <http://www.ncbi.nlm.nih.gov/pubmed/14739312>.*
(Continued)

*Primary Examiner* — Yara B Green
(74) *Attorney, Agent, or Firm* — Sughrue Mion, PLLC

(57) ABSTRACT

A radiographic imaging apparatus includes a radiation irradiator configured to irradiate radiation to an object; a radiation detector configured to detect an intensity of the radiation passing through the object; and a loader configured to load the object, and at least one of a movement speed of the loader and a range of radiation irradiation of the radiation irradiator is changed according to a change in the intensity of the radiation, when the change in the intensity of the radiation is greater than or equal to a threshold value.

24 Claims, 23 Drawing Sheets

(51) Int. Cl.
*A61B 6/03* (2006.01)
*A61B 6/06* (2006.01)

(52) U.S. Cl.
CPC ............ *A61B 6/0457* (2013.01); *A61B 6/405* (2013.01); *A61B 6/545* (2013.01); *A61B 6/06* (2013.01); *A61B 6/4291* (2013.01)

(56) References Cited

U.S. PATENT DOCUMENTS

| | | | |
|---|---|---|---|
| 6,754,299 B2 * | 6/2004 | Patch | A61B 6/032 378/15 |
| 7,848,790 B2 * | 12/2010 | Pan | A61B 6/032 378/15 |
| 2005/0008115 A1 * | 1/2005 | Tsukagoshi | A61B 6/032 378/4 |
| 2006/0039536 A1 * | 2/2006 | Nishide | A61B 6/06 378/151 |
| 2006/0109954 A1 * | 5/2006 | Gohno | A61B 6/032 378/98.12 |
| 2006/0177002 A1 | 8/2006 | Toth et al. | |
| 2014/0205071 A1 * | 7/2014 | Ikarashi | H01J 35/08 378/111 |

FOREIGN PATENT DOCUMENTS

| | | |
|---|---|---|
| KR | 1020140064597 A | 5/2014 |
| KR | 1020140115409 A | 10/2014 |

OTHER PUBLICATIONS

Communication dated Apr. 19, 2016, issued by the Korean Intellectual Property Office in counterpart Korean Application No. 10-2014-0147465.

* cited by examiner

| ATTENUATION INFORMATION | TUBE POTENTIAL (kVp) | WIDTH OF EQUINVALENT OBJECT(cm) |
|---|---|---|
| 2a | 50 | 90 |
| 4a | 50 | 60 |
| 6a | 50 | 35 |
| ⋮ | ⋮ | ⋮ |

RADIOGRAPHIC IMAGING APPARATUS AND METHOD OF CONTROLLING THE SAME

CROSS-REFERENCE TO RELATED APPLICATION

This application claims priority from Korean Patent Application No. 10-2014-0147465, filed on Oct. 28, 2014, in the Korean Intellectual Property Office, the disclosure of which is incorporated herein in its entirety by reference.

BACKGROUND

1. Field

Apparatuses and methods consistent with exemplary embodiments relate to a radiographic imaging apparatus for capturing an object using radiation, and a method of controlling the same.

2. Description of the Related Art

A radiographic imaging apparatus is an imaging apparatus which captures an internal region of an object using a characteristic that radiation, such as X-rays, are absorbed by or transmitted through the object according to characteristics of materials included in the object. The radiographic imaging apparatus may receive radiation which is transmitted through the object or generated inside the object, generate a radiographic image based on an electrical signal which is output according to the received radiation, and provide an image with respect to an internal region of the object to a user.

Since a structure of the internal region of the object is easily identified when the radiographic imaging apparatus is used, the radiographic imaging apparatus has been used in various industrial fields. For example, the radiographic imaging apparatus is used to detect a lesion of a human body or the like in hospitals, and also used to detect an internal structure of an object or a part in factories, etc. Further, the radiographic imaging apparatus is used to check the inside of a baggage in airport checkpoints, etc.

Examples of the radiographic imaging apparatus may include a digital radiography (DR) apparatus, a computed tomography (CT) apparatus, a full field digital mammography (FFDM) apparatus, etc.

SUMMARY

One or more exemplary embodiments provide a radiographic imaging apparatus capable of obtaining a radiographic image having a quality desired by a user while minimizing a radiation exposure dose of an object according to a zone of the object, and a method of controlling the same.

One or more exemplary embodiments also provide a radiographic imaging apparatus capable of obtaining higher image quality while minimizing a radiation exposure dose of an object, and a method of controlling the same.

Additional aspects of the invention will be set forth in part in the description which follows and, in part, will be obvious from the description, or may be learned by practice of the exemplary embodiments.

According to an aspect of an exemplary embodiment, a radiographic imaging apparatus includes: a radiation irradiator configured to irradiate radiation to an object; a radiation detector configured to detect an intensity of the radiation passing through the object; and a loader configured to load the object, wherein at least one of a movement speed of the loader and a range of radiation irradiation of the radiation irradiator is changed according to a change in the intensity of the radiation, when the change in the intensity of the radiation is greater than or equal to a threshold value.

The apparatus may further include a controller configured to obtain a current tube current with respect to one or more zones of the object, based on the intensity of the radiation in the one or more zones of the object.

The controller may be configured to determine a next tube current of a zone, in which the change in the intensity of the radiation is greater than or equal to the threshold value, according to the change in the intensity of the radiation, and the radiation irradiator may be configured to irradiate the radiation to the object corresponding to the next tube current of the zone.

The at least one of the movement speed of the loader and the range of the radiation irradiation may be changed while maintaining a substantially constant ratio of a value of the movement speed of the loader to a value of the range of the radiation irradiation.

The apparatus may further include a controller configured to determine a next tube current with respect to one or more zones of the object, wherein: the radiation irradiator is configured to irradiate the radiation to a zone of the object according to a next tube current determined with respect to the zone; and the controller is configured to maintain a total amount of the next tube current with respect to the one or more zones to be substantially constant.

The controller may determine one or more equivalent objects corresponding to the one or more zones of the object based on the intensity of the radiation of the object, a width of the one or more zones being determined based on a width of a corresponding equivalent object.

The controller may be configured to obtain an average value of the current tube current obtained with respect to one or more zones, and the controller may be configured to determine a next tube current of a zone based on the average value of the current tube current when the change in the intensity of the radiation is smaller than the threshold value.

The movement speed of the loader may be changed inversely proportional to the change in the intensity of the radiation, when the change in the intensity of the radiation is greater than or equal to the threshold value.

The range of the radiation irradiation of the radiation irradiator may be changed inversely proportional to the change in the intensity of the radiation, when the change in the intensity of the radiation is greater than or equal to the threshold value.

A number of rotations of the radiation irradiator may be changed according to the change in the intensity of the radiation, when the change in the intensity of the radiation is greater than or equal to the threshold value.

The apparatus may further include a controller configured to obtain one or more zones of the object by dividing the object based on the intensity of the radiation.

The apparatus may further include an input unit configured to receive, from a user, an input of at least one of an image quality, the range of the radiation irradiation, the movement speed of the loader, and a pitch.

According to an aspect of another exemplary embodiment, a method of controlling a radiographic imaging apparatus includes: irradiating radiation to an object; detecting an intensity of the radiation passing through the object; and controlling at least one of a movement speed of a loader configured to load the object and a range of radiation irradiation according to a change in the intensity of the radiation, when the change in the intensity of the radiation is greater than or equal to a threshold value.

The controlling may include dividing the object into one or more zones based on the intensity of the radiation; and controlling the at least one of the movement speed of the loader and the range of the radiation irradiation according to the change in the intensity of the radiation with respect to a zone of the object, when the change in the intensity of the radiation in the zone is greater than or equal to the threshold value.

The method may further include: obtaining a current tube current with respect to one or more zones of the object based on the intensity of the radiation; and determining a next tube current of a zone, in which the change in the intensity of the radiation is greater than or equal to the threshold value, according to the change in the intensity of the radiation.

The controlling may include controlling at least one of the movement speed of the loader configured to load the object and the range of the radiation irradiation according to the change in the intensity of the radiation, while maintaining a substantially constant ratio of a value of the movement speed of the loader to a value of the range of the radiation irradiation.

The method may further include obtaining a current tube current of each zone of the object based on an average value of the intensity of the radiation in the each zone of the object.

The controlling may include performing control such that the movement speed of the loader is changed inversely proportional to the change in the intensity of the radiation with respect to a zone of the object, when the change in the intensity of the radiation in the zone is greater than or equal to the threshold value.

The controlling may include performing control such that the range of the radiation irradiation is changed inversely proportional to the change in the intensity of the radiation with respect to a zone of the object, when the change in the intensity of the radiation in the zone is greater than or equal to the threshold value.

The method may further include, obtaining one or more zones of the object by dividing the object based on the intensity of the radiation.

According to an aspect of still another exemplary embodiment, a radiographic imaging apparatus includes: a radiographic imaging unit configured to obtain a radiographic image with respect to an object; and a processor configured to obtain attenuation information of the object based on the radiographic image and obtain one or more zones of the object by dividing the object based on the attenuation information, wherein the processor is configured to change at least one of parameters for driving the radiographic imaging unit with respect to a zone of the object based on a change in the attenuation information in the corresponding zone.

The parameters may include at least one of tube currents with respect to one or more zones, a movement speed of a loader configured to load the object, a range of radiation irradiation, a pitch, a number of rotations of a gantry, and an image quality level, the image quality level comprising at least one of a noise ratio, a resolution, a contrast ratio, and a sharpness.

The processor may be configured to reduce at least one of the movement speed of the loader and the range of the radiation irradiation with respect to a certain zone of the object, when the change in the attenuation information in the certain zone is greater than or equal to a threshold value.

The processor may be configured to: obtain a current tube current with respect to the one or more zones based on the attenuation information, when the change in the attenuation information in a first zone of the object is smaller than a threshold, determine a next tube current based on an average value of a current tube current with respect to the first zone of the object, and control the radiographic imaging unit to obtain a second radiographic image with respect to the first zone of the object by using the next tube current.

The processor may be configured to: obtain a current tube current with respect to the one or more zones based on the attenuation information, when the change in the attenuation information in a second zone is equal to or greater than a threshold, divide the second zone into a plurality of sub-zones and determine a plurality of next tube currents for the plurality of sub-zones, respectively, based on an average value of the current tube current with respect to each sub-zone of the object, and control the radiographic imaging unit to obtain a second radiographic image with respect to the second zone of the object by using the plurality of next tube currents.

A number of the plurality of sub-zones obtained by dividing the second zone may be proportional to a size of the change in the attenuation information in the second zone.

The processor may be configured to obtain the one or more zones of the object by using a lookup table, the lookup table comprising data indicating a relationship between a width of an equivalent object and the attenuation information, a width of the one or more zones being determined based on a width of a corresponding equivalent object.

BRIEF DESCRIPTION OF THE DRAWINGS

The above and/or other aspects will become more apparent by describing certain exemplary embodiments with reference to the accompanying drawings, in which:

FIG. 9 is an example of a lookup table describing a relation between attenuation information of radiation and equivalent objects;

DETAILED DESCRIPTION

Figure 1:
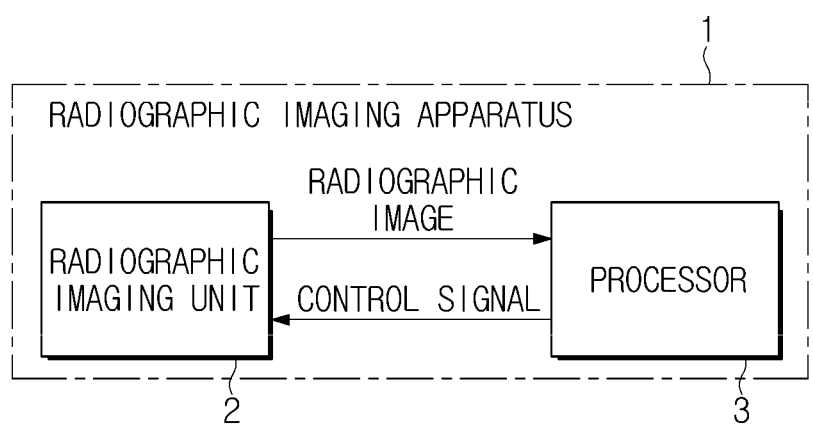
FIG. 1 is a schematic diagram of a radiographic imaging apparatus in accordance with an exemplary embodiment.

Certain exemplary embodiments are described in greater detail below with reference to the accompanying drawings. The inventive concept may, however, be embodied in many different forms and should not be construed as limited to the exemplary embodiments set forth herein. Rather, these exemplary embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

A radiographic imaging apparatus according to exemplary embodiments will be described with reference to FIGS. 1 to 14. FIG. 1 is a schematic diagram of the radiographic imaging apparatus in accordance with an exemplary embodiment. Referring to FIG. 1, the radiographic imaging apparatus 1 may include a radiographic imaging unit 2 which obtains a radiographic image with respect to an object, and a processor 3 which controls operations of the radiographic imaging unit 2.

The radiographic imaging apparatus 1 may include various radiation apparatuses capable of capturing the object using radiation. For example, the radiographic imaging apparatus 1 may include a digital radiography (DR) apparatus, a full field digital mammography (FFDM) apparatus, a computed tomography (CT) apparatus, etc. The radiographic imaging apparatus 1 may include apparatuses capable of obtaining an image of an internal region of the object using radiation, in addition to the above-described apparatuses. The radiographic imaging apparatus 1 may refer to a physical element capable of obtaining a radiographic image, and also to a combination of a plurality of elements capable of obtaining the radiographic image by connecting through a wired or wireless communication network and operating in association with each other.

The object may include a living entity such as a human body or an animal, or a non-living entity such as a part or a luggage. Further, the object may include a phantom. The object may be an entire part of a specific object, or a part of the specific object. For example, the object may be a specific part of the human body, for example, a leg, an arm, or an organ.

The radiographic imaging unit 2 may perform a function of obtaining a radiographic image of the object using radiation. The radiographic imaging unit 2 may irradiate the object with the radiation, receive the radiation transmitted through the object, convert the received radiation into an electrical signal, and obtain the radiographic image. The radiographic image may be raw data. The radiographic imaging unit 2 may include a radiation source and a detector in order to obtain the radiographic image. The radiation source may include a radiation tube, and the radiation tube may be controlled by an applied tube current and a tube potential. The radiographic image obtained by the radiographic imaging unit 2 may be transferred to the processor 3.

The processor 3 may generate a control signal for controlling operations of the radiographic imaging unit 2 based on the radiographic image transferred from the radiographic imaging unit 2, and transfer the generated control signal to the radiographic imaging unit 2. The processor 3 may be referred to as a "controller." The processor 3 may be implemented by one or more semiconductor chips which are provided in the radiographic imaging apparatus 1. Further, the processor 3 may be implemented by using one or more semiconductor chips which are provided in a workstation which may be implemented as a computer or the like that is positioned outside the radiographic imaging apparatus 1.

Although an exemplary embodiment in which the processor 3 generates the control signal based on the radiographic image transferred from the radiographic imaging unit 2 of the radiographic imaging apparatus 1 is illustrated in FIG. 1, the radiographic image based on which the control signal is generated may be not limited to the radiographic image generated from the radiographic imaging unit 2. In some exemplary embodiments, the processor 3 may generate the control signal for controlling the radiographic imaging unit 2 by receiving the radiographic image obtained from an imaging apparatus other than the radiographic imaging apparatus 1. In this case, the imaging apparatus other than the radiographic imaging apparatus 1 may be the same type of imaging apparatuses or different types of imaging apparatuses from the type of the radiographic imaging apparatus 1. Further, the other imaging apparatus may include a positron emission tomography (PET) apparatus or a single photon emission computed tomography (SPECT) apparatus, in addition to the above-described DR apparatus, FFDM apparatus, or CT apparatus.

The processor 3 may determine an equivalent object corresponding to the object which is captured by the radiographic imaging unit 2. The equivalent object may include a water-equivalent object (WEO) or a water-equivalent object phantom. The WEO may refer to a real or virtual object comprising water and having substantially the same predetermined characteristic as a predetermined characteristic of the object. Here, the characteristic may include an attenuation ratio. The processor 3 may determine the equivalent object with reference to reference data which is theoretically or experientially obtained. The tube potential and the attenuation ratio of the object, which are used to irradiate the radiation in the radiographic imaging unit 2, may be used to determine the equivalent object. The equivalent object may be determined for each specific zone of the radiographic image.

When the equivalent object is determined, the processor 3 may obtain a tube current with respect to one or more zones of the object based on set image quality and the determined equivalent object. One or more equivalent objects may be obtained for each specific zone, and the tube current of each zone may be obtained as the tube current of each equivalent object. Further, one or more tube currents may be obtained with respect to a certain zone.

The processor 3 may obtain one or more tube currents with reference to the reference data which is theoretically or experientially obtained. In this case, the processor 3 may also obtain one or more tube currents according to the desired quality of the radiographic image.

When one or more tube currents are obtained, the processor 3 calculates a changed value of attenuation information of the object for each zone, and determines whether the changed value is greater than or equal to a threshold value. In this case, the changed value of the attenuation information may be a gradient of the attenuation information according to a position of the object, and the attenuation information may be represented by an intensity or an attenuation ratio of the radiation transmitted through the object. The threshold value is a reference value of the attenuation information for determining when the attenuation information is rapidly changed, and the threshold value may be a value which is input or is previously stored in a manufacturing process or during usage of the radiographic imaging apparatus 1. When one or more tube currents with respect to a certain zone is obtained, the processor 3 may calculate a changed value of the tube current for each zone instead of the changed value of the attenuation information of the object, and determine whether the changed value is greater than or equal to the threshold value. Hereinafter, it is assumed that "a changed value" is referred to as, for example, the changed value of the attenuation information, for convenience of descriptions.

With respect to the zone in which the changed value of the attenuation information is smaller than the threshold value, the processor 3 drives the radiographic imaging unit 2 based on a preset parameter. The preset parameter may include various parameters related to the radiographic imaging apparatus 1, such as an average value of the tube current with respect to one or more zones of the object which is obtained based on the set image quality and the determined equivalent object, a table feed, a radiation irradiation region (or a range of radiation irradiation), a pitch, the number of rotations of a gantry 140 to be described below (see FIG. 4), a quality level of the image, or the like, and may be a value which is input or is previously stored in a manufacturing process or during usage of the radiographic imaging apparatus 1. The table feed denotes a movement speed of a loader 97 to be described below, the radiation irradiation region denotes a region which is radiated by a first collimator 130 to be described below, and the pitch denotes a ratio of the table feed to a size of the radiation irradiation region. Further, when one or more tube currents are obtained with respect to each zone, the tube current with respect to each zone, which is determined to drive the radiographic imaging unit 2, may be an average value of one or more tube currents in each zone.

With respect to the zone in which the changed value is greater than or equal to the threshold value, the processor 3 may newly obtain the parameter of the zone according to the changed value. In this case, the processor 3 may newly obtain one or more tube currents with respect to the zone, determine the table feed and the radiation irradiation region, and maintain a constant ratio of the table feed to the size of the radiation irradiation region in the zone.

Further, when one or more tube currents are obtained with respect to a certain zone, the radiographic imaging apparatus 1 may obtain a tube current with respect to a sub-zone of the zone in which the changed value is greater than or equal to the threshold value. That is, the zone may be divided into sub-zones and tube current may be individually obtained according to each sub-zone rather than obtained as an average value of one or more tube currents with respect to the zone, even when the zone has a larger changed value of the attenuation information.

Further, the processor 3 may determine the table feed such that the table feed is reduced to perform inspection on the zone of the object which requires higher image quality (or the zone in which the changed value of the attenuation information is greater than or equal to the threshold value). Also, the processor 3 may determine the radiation irradiation region such that the size of the radiation irradiation region is reduced proportional to the table feed in order to maintain a preset total radiation exposure dose of the object. That is, the processor 3 may determine the table feed and the radiation irradiation region so that a total sum of the obtained or determined tube current (hereinafter, a total amount of tube current) is constantly maintained with respect to one or more zones, and thus may constantly maintain the total radiation exposure dose requested by a user. The processor 3 may maintain the constant ratio of the table feed to the radiation irradiation region to maintain the total radiation exposure dose, calculate and obtain the parameter, using a separate formula depending on embodiments, and drive the radiographic imaging unit 2 based on the obtained parameter. According to an exemplary embodiment, the parameter used to drive the radiographic imaging unit 2 may be input by the user through a separate input unit 212.

Further, the processor 3 may control the radiographic imaging unit 2 according to the obtained or input parameter.

Figure 2:
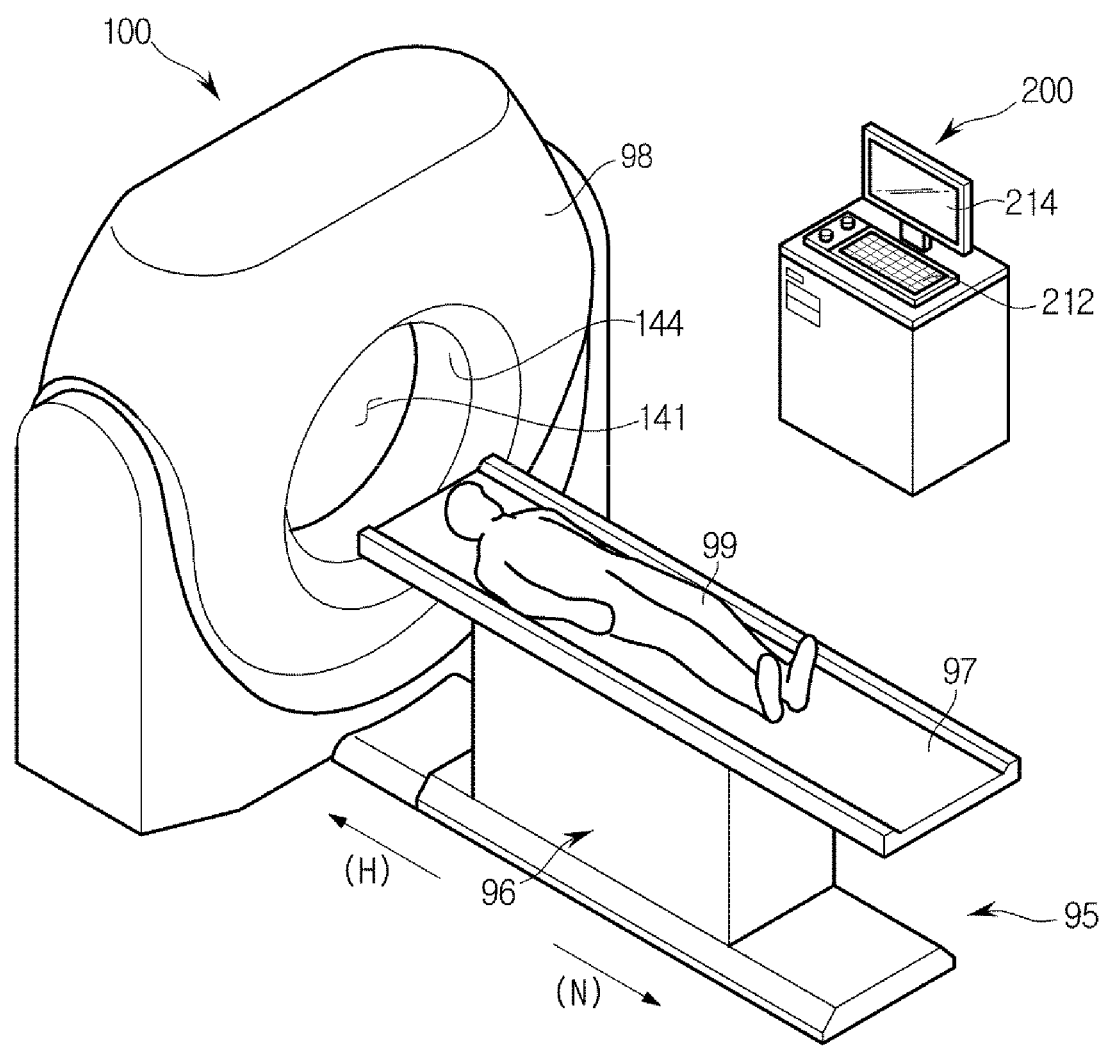
FIG. 2 is a view of a computed tomography (CT) apparatus in accordance with an exemplary embodiment.
Figure 3:
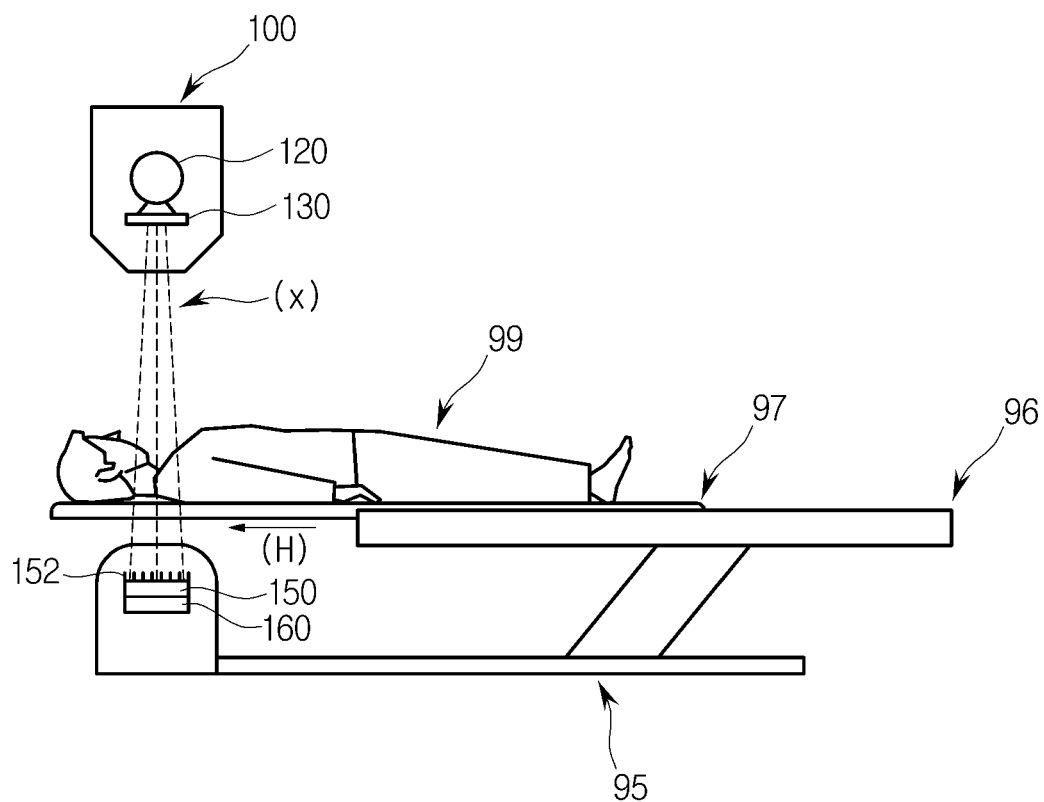
FIG. 3 is a view for describing a CT apparatus in accordance with an exemplary embodiment.
Figure 4:
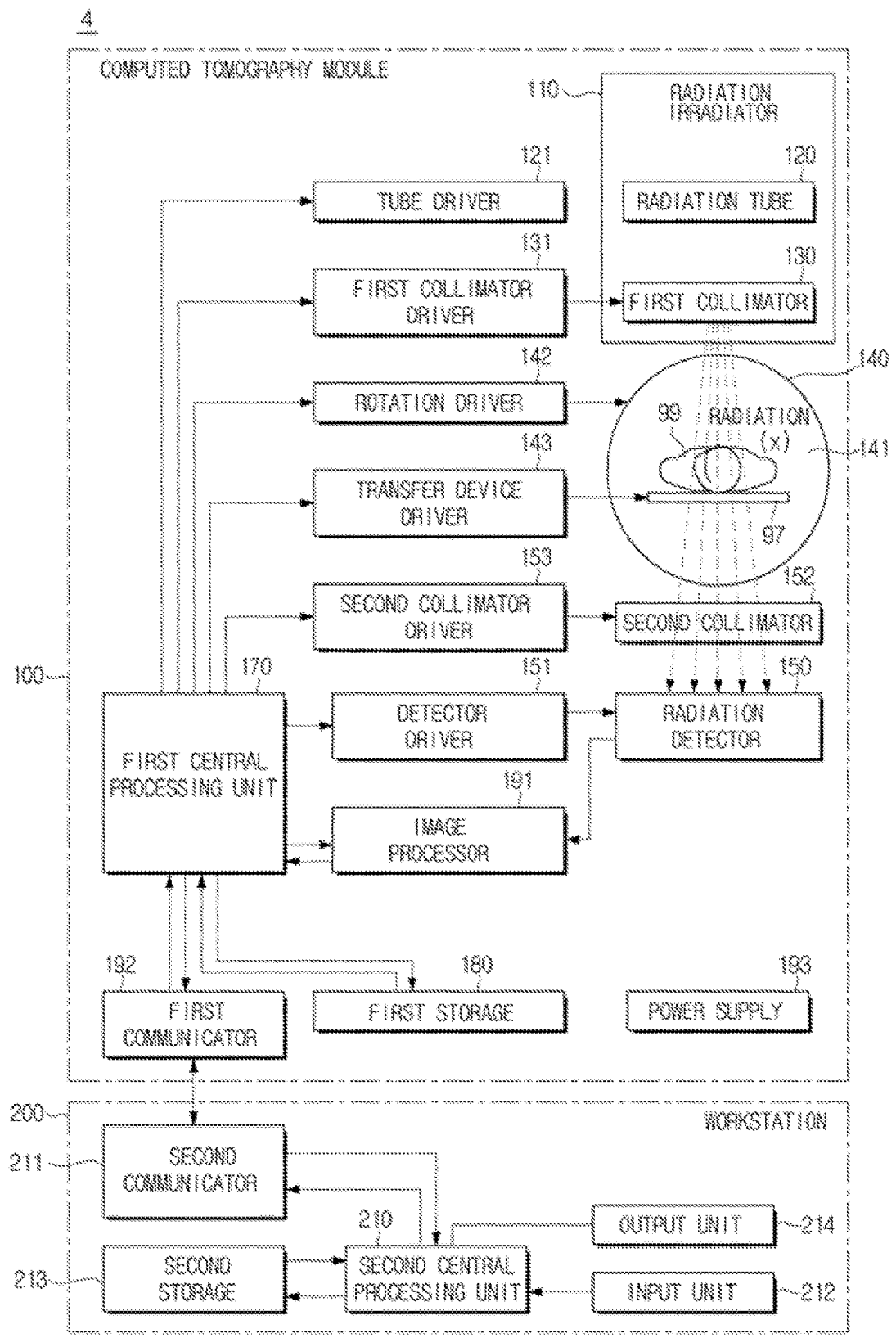
FIG. 4 is a schematic diagram of a CT apparatus in accordance with an exemplary embodiment.

Hereinafter, a CT apparatus will be described as an example of the radiographic imaging apparatus with reference to FIGS. 2 to 14. FIG. 2 is a view of the CT apparatus in accordance with an exemplary embodiment, FIG. 3 is a view for describing a CT apparatus in accordance with an exemplary embodiment, and FIG. 4 is a schematic diagram of a CT apparatus in accordance with an exemplary embodiment. Referring to FIGS. 2 to 4, a CT apparatus 4 may include a CT module 100 which captures the object and a workstation 200 which controls the CT module 100, etc. The CT module 100 and the workstation 200 may be connected through a wired communication network or a wireless communication network.

Hereinafter, the CT module 100 according to an exemplary embodiment will be described.

As shown in FIGS. 2 and 3, the CT module 100 may include an external housing 98 in which various parts of the CT apparatus 4 are embedded. A bore 141 in a circular shape or a shape similar to the circular shape may be formed at a part of the external housing 98, for example, a center thereof. The external housing 98 may include a gantry 140 which may be rotatable in at least one direction. The gantry 140 may be installed along an inner peripheral surface 144 of the bore 141. A radiation irradiator (or a radiation transmitter) 110 and a radiation detector 150 may be installed in the gantry 140. When the gantry 140 rotates, the radiation irradiator 110 and the radiation detector 150 may also rotate together with the gantry 140.

The CT module 100 may include a transfer device 95 which transfers an object 99 toward the inside of the bore 141. The transfer device 95 may include a loader 97 which loads the object 99 and a support 96 which supports the loader 97. The loader 97 may move at a predetermined speed in a first direction (H) toward the bore 141 of the external housing 98 by an operation of a transfer device driver 143 such as a motor, an actuator, etc. The predetermined speed at which the loader 97 moves may be fixed or variable. The transfer device driver 143 may be provided inside the support 96. A wheel or a rail may be provided inside the loader 97 or the support 96 so that the loader 97 may move according to the operation of the transfer device driver 143. The object 99 loaded on the loader 97 may also be transferred toward the inside the bore 141 according to the movement of the loader 97. After the capturing of the object 99 is ended, the loader 97 may move in a second direction (N), opposite to the first direction (H), to transfer the object 99 toward the outside of the bore 141.

Referring to FIGS. 3 and 4, the CT module 100 may include the radiation irradiator 110 which irradiates the inside of the bore 141 with radiation, the radiation detector 150, a second collimator 152, drivers including a tube driver 121, a first collimator driver 131, a rotation driver 142, the transfer device driver 143, and a second collimator driver 153 which drive corresponding parts, respectively, a first central processing unit (CPU) 170, a first storage 180, an image processor 191, a first communicator 192, and a power supply 193, in addition to the bore 141, the gantry 140, and the transfer device 95 including the loader 97. Some of the above elements may be omitted in the CT apparatus 4 or may be provided in the workstation 200 in some exemplary embodiments.

The radiation irradiator 110 may include a radiation tube 120 which generates and irradiates radiation and a first collimator 130 which guides the irradiated radiation.

Figure 5:
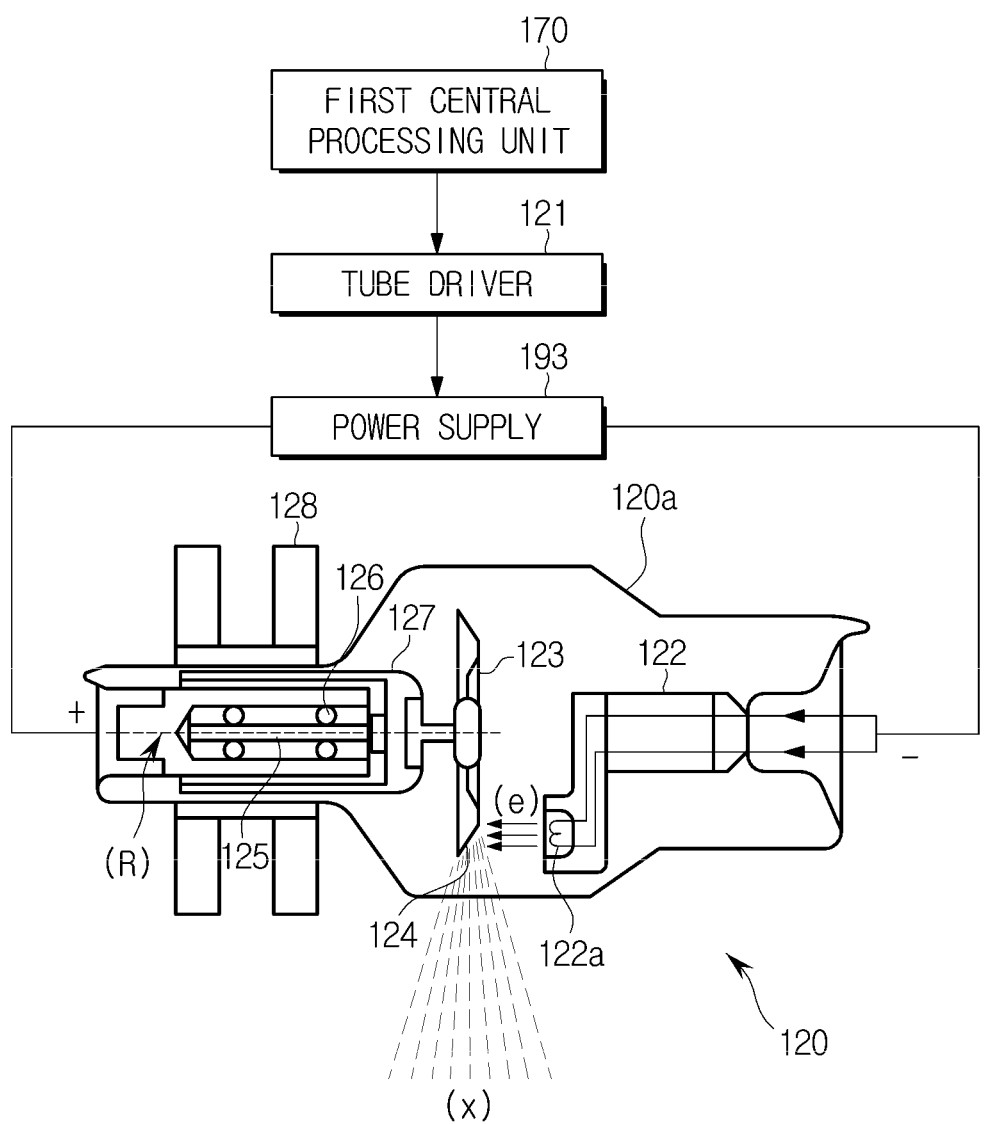
FIG. 5 is a view of a CT module including a radiation tube in accordance with an exemplary embodiment.

FIG. 5 is a view of a CT module including a radiation tube in accordance with an exemplary embodiment. Referring to FIG. 5, the radiation tube 120 of the CT module 100 may be electrically connected to an external power supply 193. The external power supply 193 may or may not apply a predetermined voltage and current to the radiation tube 120 according to controls of the first central processing unit 170 and the tube driver 121. When the predetermined voltage and current are applied to the radiation tube 120, the radiation tube 120 may generate a certain amount of radiation according to the applied predetermined voltage and current. In this case, a potential difference between a cathode filament 122a and an anode 123 of the radiation tube 120 is referred to as a tube potential, and a current which flows due to electrons which collide with the anode 123 is referred to as a tube current. Since a speed of the electrons is increased when the tube potential is increased, a size of energy of the generated radiation is increased accordingly. When the tube current is increased, a dose of the radiation may be increased. Therefore, by adjusting a potential and a current applied by the external power supply 193, energy spectrum and the dose of the radiation may be adjusted.

Referring to FIG. 5, the radiation tube 120 may include a tube body 120a, a cathode 122, and the anode 123. The tube body 120a may stably fix various parts while embedding the various parts which are needed to generate the radiation, such as the cathode 122 and the anode 123. Further, the tube body 120a may shield the electrons, which are generated in the cathode 122 and moved to the anode 123, such that the electrons may not leak to the outside. A higher degree of vacuum of the inside of the tube body 120a may be maintained at about $10^{-7}$ mmHg. The tube body 120a may be a glass tube comprising rigid silicate glass. Electron beams (e) may be irradiated from the cathode 122 in a direction toward the anode 123. The filament 122a in which electrons are gathered may be provided at an end portion of the cathode 122, and the filament 122a may be heated according to the applied tube potential to emit the electrons, which are densely gathered therein, to the inside of the tube body 120a. The electrons (e) emitted from the filament 122a may move in the direction toward the anode 123 while the electrons (e) are accelerated in the tube body 120a. Energy of the electrons (e) emitted to the inside of the tube body 120a may be determined according to the tube potential. The filament 122a of the cathode 122 may comprise a metal such as tungsten (W). In some exemplary embodiments, a carbon nano tube instead of the filament 122a may be provided in the cathode 122. A predetermined amount of radiation may be generated in the anode 123. A target surface 124 with which the electrons (e) collide may be formed on the anode 123. Radiation (x) having energy corresponding to the tube potential applied according to rapid deceleration of the electrons (e) may be generated in the target surface 124. Since the target surface 124 is cut in a predetermined direction as shown in FIG. 5, the generated radiation (x) may be mainly emitted in a predetermined direction. The anode 123 may comprise a metal, such as copper (Cu), or the like, and the target surface 124 may comprise a metal such as tungsten (W), chromium (Cr), iron (Fe), nickel (Ni), etc.

According to an exemplary embodiment, as shown in FIG. 5, the anode 123 may be a rotary anode having a disc shape. An end part of the rotary anode 123 may be cut at a predetermined angle, and the target surface 124 may be formed at a cut portion of the end part of the rotary anode 123. The rotary anode 123 may rotate at a predetermined speed around a predetermined axis (R). In order to rotate the rotary anode 123, the radiation tube 120 may include a stator 128 which generates a rotating magnetic field, a rotor 127 which rotates the rotary anode 123 by rotating according to the rotating magnetic field generated in the stator 128, a bearing 126 which is rotated according to the rotation of the rotor 127, and a shaft member 125 which is positioned along a rotation axis (R) of the rotary anode 123. The rotor 127 may comprise a permanent magnet. In the rotary anode 123, a focus size is reduced while a heat accumulation rate is increased than in a fixed anode, and thus a clearer radiographic image may be obtained. According to another exemplary embodiment, the anode 123 may be a fixed anode in a cylinder shape in which a surface on which the electron beams are radiated is cut at a predetermined angle. In this case, the target surface 124 may be formed at cut parts of the fixed anode. The radiation irradiator 110 may also include a plurality of radiation tubes 120 in some exemplary embodiments.

The first collimator 130 may filter radiation emitted from the radiation tube 120 to guide the radiation so that the radiation is radiated into an area in a specific direction. The first collimator 130 may include an opening through which the radiation which is radiated in the specific direction passes, and collimator blades which absorb the radiation which is radiated in different directions. The user may control an irradiation direction of the radiation and an irradiation range of the radiation using a position and a size of the opening of the first collimator 130. The collimator blades of the first collimator 130 may comprise a material capable of absorbing the radiation such as lead (Pb), etc.

Figure 6:
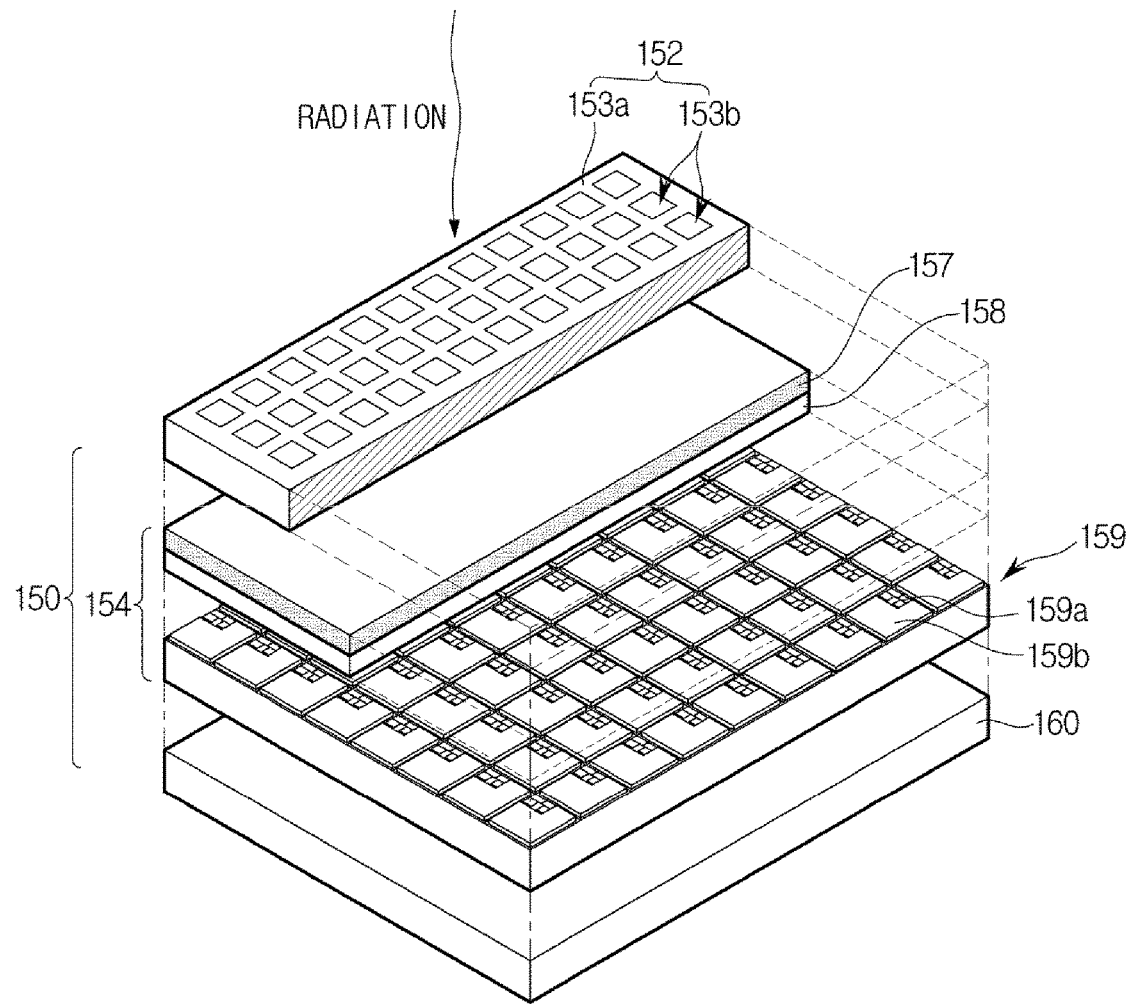
FIG. 6 is a view of a radiation detector and a second collimator in accordance with an exemplary embodiment.

FIG. 6 is a view of a radiation detector and a second collimator in accordance with an exemplary embodiment. The object 99 inside the bore 141 may be irradiated with radiation (x) irradiated from the radiation irradiator 110, and the radiation transmitted through the object 99 may pass through the second collimator 152 and reach the radiation detector 150.

The second collimator 152 may absorb the radiation which is scattered while passing through the inside of the object 99 and cause only the radiation in a specific direction reach a detection panel 154 of the radiation detector 150. The second collimator 152 may include a plurality of partitions 153a which block the radiation, and transmission holes 153b through which the radiation passes. The partitions 153a may comprise a material such as lead (Pb) to absorb the scattered or bent radiation, and the transmission holes 153b may allow the radiation which is not scattered and bent to pass therethrough.

The radiation detector 150 may receive the radiation, convert the received radiation into a corresponding electrical signal, and output the converted electrical signal. In some exemplary embodiments, the radiation detector 150 may directly convert the radiation into the electrical signal (a direct method), or may generate visible light according to the radiation and convert the visible light into the electrical signal (an indirect method). When the radiation detector 150 converts the radiation into the electrical signal according to the direct method, the radiation detector 150 may include a first electrode 157 in which the radiation is incident on a first surface thereof, a semiconductor material layer 158 installed on a second surface of the first electrode 157 on which the radiation is not incident, a detection panel 154 including a flat plate 159 installed on the semiconductor material layer 158, and a substrate 160 installed on a surface of the detection panel 154. Here, second electrodes 159*a* (or pixel electrodes) and thin film transistors 159*b* which are arranged in one or more columns on the flat plate 159 are installed on the semiconductor material layer 158. A polarity of the first electrode 157 may be a positive (+) polarity or a negative (−) polarity and a polarity of the second electrode 159*a* may be a polarity opposite to the polarity of the first electrode 157. A predetermined bias voltage may be applied between the first electrode 157 and the second electrode 159*a*. The semiconductor material layer 158 may generate predetermined charge-hole pairs according to the incident and absorption of the radiation, the generated charge-hole pairs may be moved in a direction toward the first electrode 157 or the second electrode 159*a* according to the polarities of the first electrode 157 and the second electrode 159*a*. The second electrode 159*a* may receive a hole or negative charge, which is transmitted from the semiconductor material layer 158, and output an electrical signal. The thin film transistor 159*b* may read the electrical signal transmitted from the corresponding second electrode 159*a*. In this case, the corresponding second electrode 159*a* and the thin film transistor 159*b* may be installed in a complementary metal oxide semiconductor (CMOS) chip.

When the radiation detector 150 converts the radiation into the electrical signal according to the indirect method, a phosphor screen which outputs the visible light corresponding to the received radiation may be disposed between the second collimator 152 and the detection panel 154, and a photo diode instead of the second electrode 159*a* may be installed on the flat plate 159 to convert the visible light into the electrical signal. The detection panel 154 may include a scintillator which outputs a predetermined visible light photon and a photodiode which detects the visible light photon according to the radiation. According to an exemplary embodiment, the radiation detector 150 may be a photon counting detector (PCD). The substrate 160 may be attached to the surface of the detection panel 154 to control various operations of the detection panel 154 or store the electrical signal which outputs from the detection panel 154.

The electrical signal obtained by the radiation detector 150 may be transferred to the image processor 191. The image processor 191 may generate an image which may be easily recognized as an internal structure of the object 99 by the user, based on the obtained electrical signal, and perform an additional image processing if needed. The image processor 191 may be implemented as a graphic processing unit (GPU). The GPU may include a semiconductor chip such as a graphic chip. Various operations or functions of the image processor 191 may be performed by the first central processing unit 170 or a second central processing unit 210 of the workstation 200. In this case, the image processor 191 may be omitted. The generated radiographic image may be transferred to the first central processing unit 170 or the first storage 180. The radiographic image may be transferred to the workstation 200 through the first communicator 192 of the CT module 100 and a second communicator 211 of the workstation 200.

Figure 7:
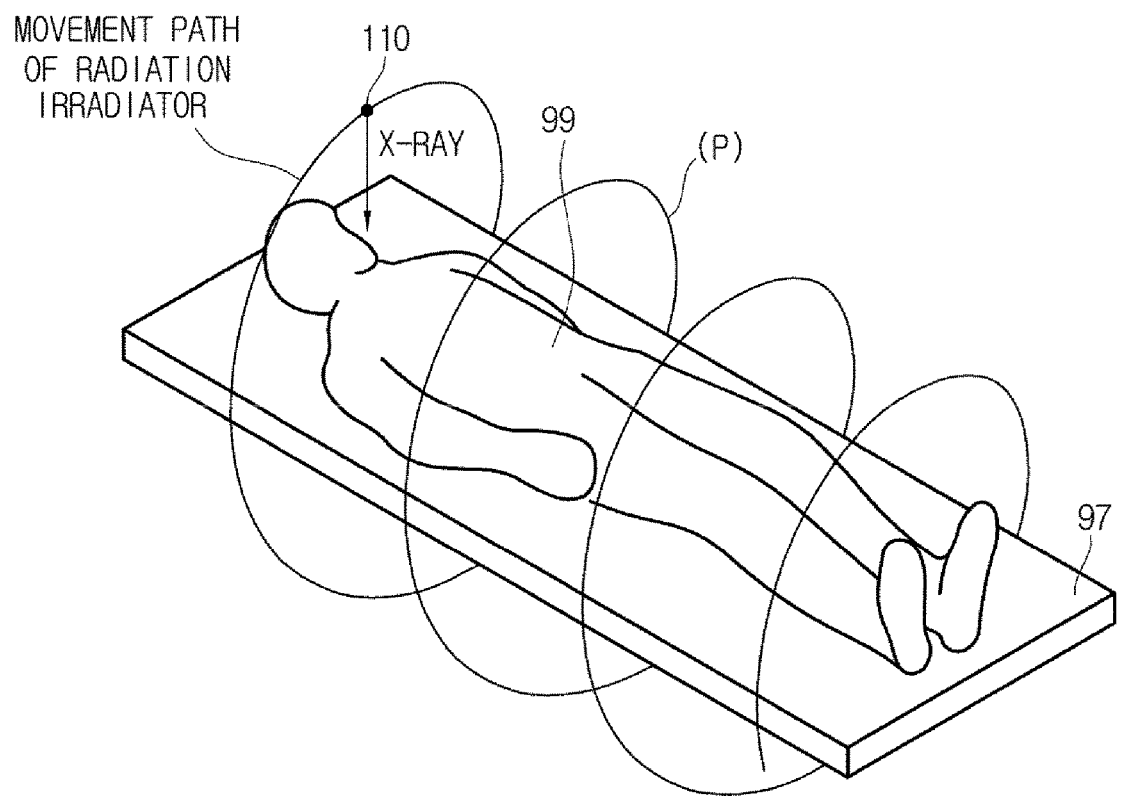
FIG. 7 is a view for describing radiography of a CT apparatus.

FIG. 7 is a view for describing radiography of a CT apparatus. The radiation irradiator 110 and the radiation detector 150 may repeatedly capture a radiographic image of the object 99 while rotating by the gantry 140. As described above, since the object 99 is moved to the inside of the bore 141 by the transfer device 95 at a predetermined speed, the radiation irradiator 110 and the detector 150 may perform capturing of the object 99 while rotating and moving in a spiral shape (P) around the object 99, as shown in FIG. 7. Therefore, a tomographic image with respect to the body of the object 99 may be captured. On the other hand, the object 99 on the loader 97 may be moved at a specific speed in any zone of the object. When a speed at which the object 99 is moved in a first zone is smaller than a speed at which the object 99 is moved in a second zone, a rotation number of the gantry 140 in the first zone may be greater than the number of rotations in the second zone. That is, the movement speed of the object 99 may be inversely proportional to the rotation number of the gantry 140.

The CT module 100 may include the first central processing unit 170 which controls each part of the CT module 100. The first central processing unit 170 may generate a control command according to a previously stored setting or a user selection, and may transmit the generated control command to the radiation irradiator 110, the second collimator 152, the radiation detector 150, the image processor 191, the gantry 140, the transfer device 143, or the like, to control overall operations such as radiography and/or image processing of the CT module 100. The first central processing unit 170 may transmit the control command to each driver 121, 131, 142, 143, and 153 to control an operation of each component. The first central processing unit 170 may transmit the control command to each driver 121, 131, 142, 143, and 153 when needed so that each component operates according to the control command. The first central processing unit 170 may perform some or all of the function of the processor 3 described in FIG. 1. The first central processing unit 170 may perform calculation or processing, and may be implemented by one or more semiconductor chips on a printed circuit board, etc.

The tube driver 121 may apply a predetermined tube potential and a predetermined tube current to the radiation tube 120 such that a switch connected to the radiation tube 120 is turned on and/or off according to the control command of the first central processing unit 170. The first collimator driver 131 may operate the first collimator 130 such that an opening of the first collimator 130 expands or is reduced according to the control command of the first central processing unit 170. The rotation driver 142 may rotate the gantry 140 according to the control command of the first central processing unit 170. According to rotation of the gantry 140, the radiation irradiator 110, the first collimator 130, the second collimator 152, and the radiation detector 150 may be rotated together with the gantry 140. The transfer device driver 143 may operate according to the control command of the first central processing unit 170 to move the loader 97 in the first direction (H) (see FIG. 3) toward the bore 141 of the external housing 98.

As describe above, the transfer device driver 143 may include a motor or an actuator. A second collimator driver 153 may operate the second collimator 152 according to the control command of the first central processing unit 170. In this case, for example, the operation of the second collimator 152 may include a position of the transmission holes 153*b* in a vertical direction or a lateral direction and changing a size of the transmission holes 153*b*. All or at least one of the above-described drivers 121, 131, 142, 143, and 153 may be omitted in some exemplary embodiments.

The first storage 180 may store various information needed for the control of the CT module 100. The first storage 180 may be installed inside the external housing 98 of the CT module 100, or outside the external housing 98. The first storage 180 may be a semiconductor memory device or a magnetic disc memory device. The first storage 180 may temporarily or non-temporarily store data.

Figure 8:
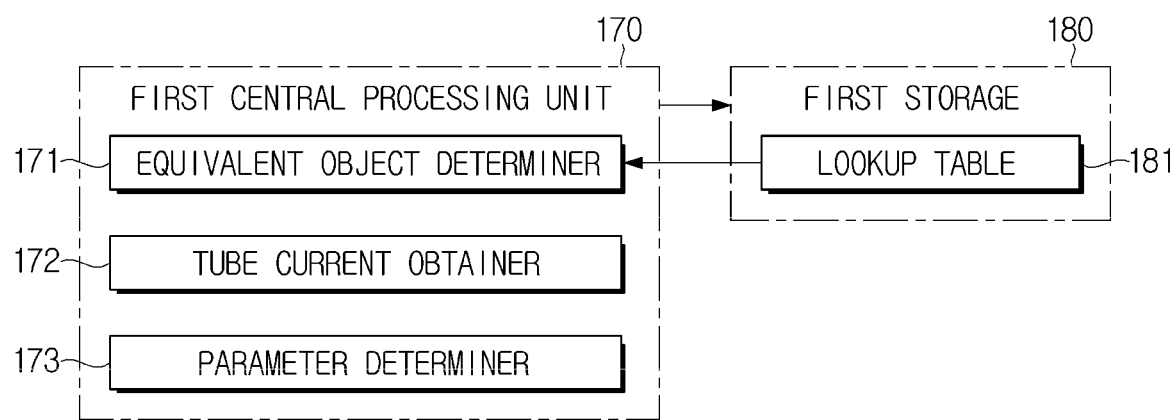
FIG. 8 is a schematic diagram illustrating a central processing unit and a storage of a CT module in accordance with an exemplary embodiment.

FIG. 8 is a schematic diagram illustrating a central processing unit and a storage of a CT module in accordance with an exemplary embodiment. The first central processing unit 170 may include an equivalent object determiner 171, a tube current obtainer 172, and a parameter determiner 173, as described in FIG. 8. The equivalent object determiner 171, the tube current obtainer 172, and the parameter determiner 173 may be implemented by a plurality of semiconductor devices physically separated from each other, respectively. Alternatively, at least a part or all of the above elements may be implemented by a single semiconductor device according to a system design.

The first storage 180 may store reference data used for control of the CT module 100. More specifically, the first storage 180 may store data in a form of a lookup table 181 as shown in FIG. 8. The lookup table 181 may include a set of data with respect to a relation between attenuation information of the object and equivalent objects. The lookup table 181 may be empirically determined or by calculation using a separate formula.

Hereinafter, a process of obtaining a control signal with respect to the CT module 100 using the first central processing unit 170 and the lookup table 181 of the first storage 180 will be described. The equivalent object determiner 171 of the first central processing unit 170 may determine an equivalent object corresponding to the object based on an obtained radiographic image. More specifically, the first central processing unit 170 may determine one or more equivalent objects corresponding to all or a part of the object using attenuation information about all or the part of the object based on a signal output from the radiation detector 150. Here, the equivalent object determiner 171 may use the radiographic image captured by the CT module 100, and may determine the equivalent object corresponding to the object using a radiographic image captured by another radiography imaging apparatus such as the DR apparatus or another CT apparatus.

An intensity of the radiation transmitted through the object may satisfy the following Equation 1.

$$I = I_0 e^{-\mu t}$$ [Equation 1]

Here, I denotes an intensity of the radiation detected by the radiation detector 150, and $I_0$ denotes an intensity of the radiation emitted from the radiation tube 120. $\mu$ denotes an attenuation factor according to a characteristic of an object, and t denotes a distance by which the radiation is transmitted through the object, that is, a width of the object. In other words, the intensity of the radiation may be determined according to an intensity $I_0$ of the radiation, the characteristic $\mu$ of each object, and the distance t by which the radiation is transmitted through the object. If an attenuation ratio ($I/I_0$) of the object is substantially the same as an attenuation ratio of an equivalent object ($I_e/I_{e0}$), a value of the exponential part ($e^{-\mu t}$) in Equation 1 for the object may also be substantially the same as an exponential part ($e^{-\mu_e t_e}$) for the equivalent object. In this case, if the equivalent objects are the same and the attenuation factor $\mu_e$ of the equivalent object is constant, the width $t_e$ of the equivalent object may be changed according to a type of the object. In other words, the equivalent objects having different widths ($t_e$) may correspond to different types of the object. Using this principle, one or more equivalent objects corresponding to all or the part of the object may be determined according to the width ($t_e$) of the equivalent objects. This means that all or the part of the object may be converted based on the width ($t_e$) of the equivalent object. If the equivalent object is a WEO, a configuration of the inside of the object may be converted based on water by using the equivalent object.

The equivalent object determiner 171 of the first central processing unit 170 may determine one or more equivalent objects having the width $t_e$ corresponding to all or the part of the object as described above. In this case, the equivalent object determiner 171 may determine one or more equivalent objects according to the tube potential and the attenuation information with reference to the lookup table 181 which includes data with respect to a relation between the attenuation information and the equivalent object.

FIG. 9 is an example of a lookup table describing a relation between attenuation information of radiation and equivalent objects in accordance with an exemplary embodiment. FIG. 9 is only given as an example and may include values different from actual measurement values. In a table shown in FIG. 9, a first column of the lookup table 181 indicates the attenuation information, which may be represented by a radiation intensity, at the tube potential of 50 kVp. When a indicates a reference value of the attenuation information, 2a refers to two times the reference value a, and 4a refers to four times the reference value a. A third column of the lookup table 181 indicates a width (cm) of a corresponding equivalent object. FIG. 9 shows only information corresponding to the tube potential of 50 kVp, however, the lookup table 181 may further include information corresponding to a tube potential of different values. Referring to FIG. 9, when the radiation intensity is 4a and the tube potential is 50 kVp, the equivalent object determiner 171 may determine the equivalent object having a width of 60 cm. The lookup table 181 may be stored based on data experimentally obtained by radiating radiation having a predetermined intensity to the object and the WEO, respectively.

Figure 10A:
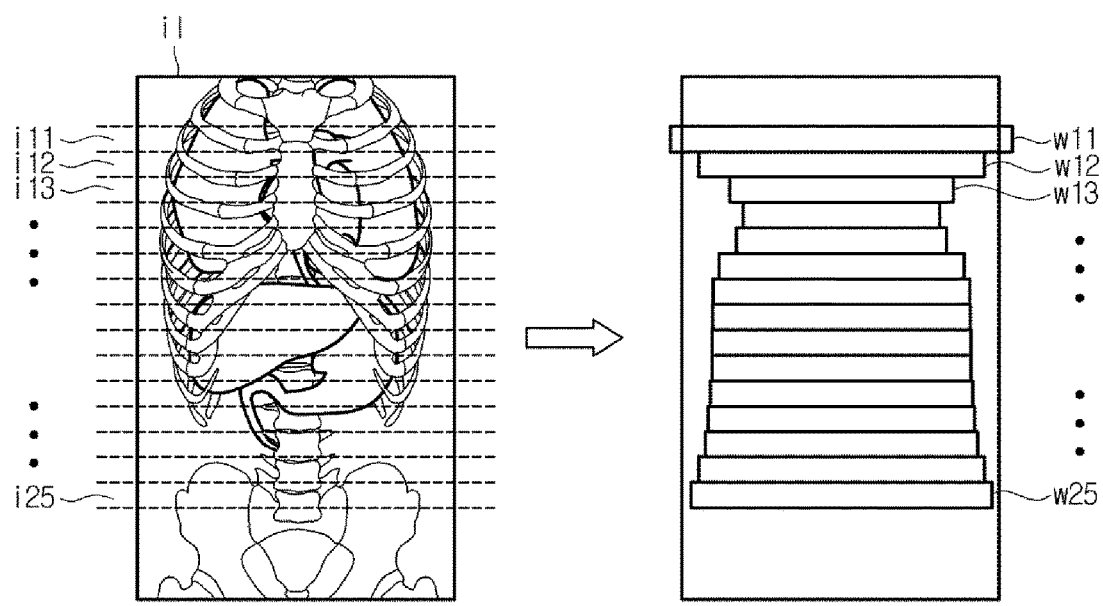
FIGS. 10A and 10B are views for describing an equivalent object corresponding to each zone of an object in accordance with exemplary embodiments.
Figure 10B:
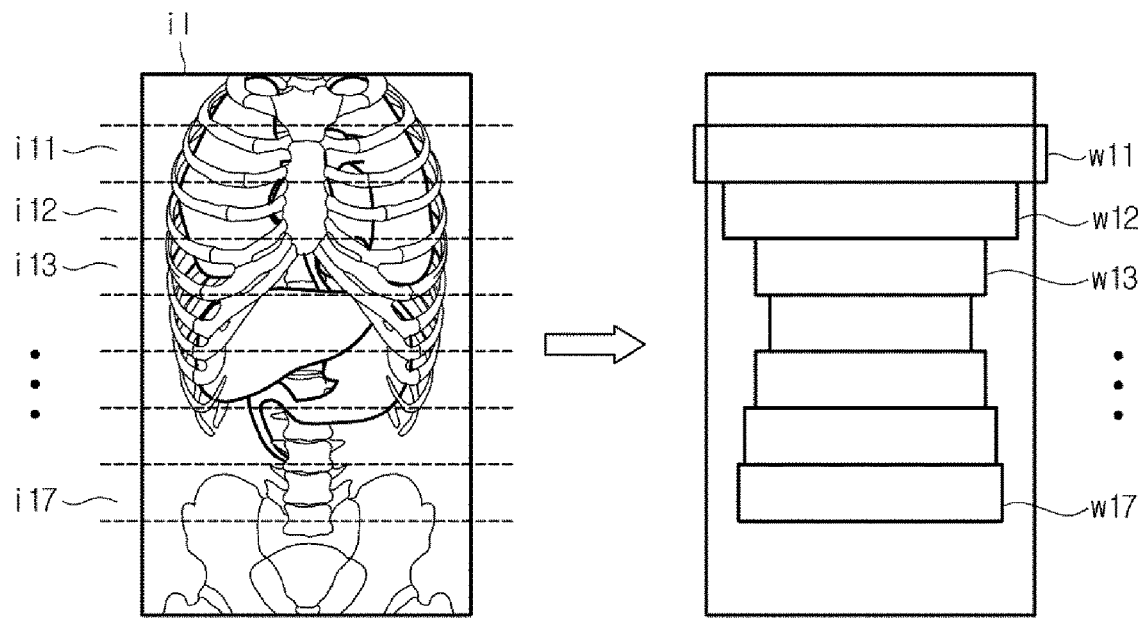

FIGS. 10A and 10B are views for describing an equivalent object corresponding to each zone of an object in accordance with exemplary embodiments. Referring to FIG. 10A, the equivalent object determiner 171 may divide a radiographic image it to predetermined zones i11, i12, i13, . . . , i25 and determine equivalent objects w11, w12, w13, . . . , w25 corresponding to the zones i11 to i25, respectively. In this case, widths $t_e$ of the equivalent objects w11 to w25 corresponding to the zones i11 to i25, respectively, may be different from each other according to a type of a composition of the object corresponding to the zones i11 to i25. For example, when a certain zone of the radiographic image i1 corresponds to an image obtained by radiation passing through a lung, the width of the equivalent object corresponding to the certain zone may be smaller than the width of another zone of the radiographic image i1.

Further, the number of zones i11 to i25 may be changed according to desired quality of the radiographic image. When the number of zones i11 to i25 is changed, the number of the equivalent objects w11 to w25 may also be changed. For example, when the desired quality of the radiographic image is reduced than that of FIG. 10A, the radiographic image i1 may be divided into zones i11, i12, i13, . . . , i17 as shown in FIG. 10B, and thus the number of equivalent objects w11, w12, w13, . . . , w17 may also be changed according to the number of the zones i11 to i17.

Further, the width $t_e$ of each of the equivalent objects w11 to w25 may be determined based on an average value of the radiation intensity for each of the zones i11 to i25. For example, referring again to FIG. 9, when the average value of the radiation intensity of the zone i13 is 6a, the width $t_e$ of the equivalent object w13 corresponding to the zone i13 may be determined to be 35 cm.

When the equivalent objects w11 to w25 with respect to the entire object or the plurality of zones i11 to i25 are determined, the tube current obtainer 172 may obtain one or more tube currents using the desired quality of the radiographic image and the determined equivalent objects.

The desired quality of the radiographic image may be input by the user using the input unit 212 of the workstation 200 or an input device such as a keyboard or a mouse provided in the CT module 100. The desired quality of the radiographic image may include a noise ratio, which is a degree of noise in the image, a resolution, a contrast ratio, sharpness, or the like. An output unit 214 of the workstation 200, for example, a display device may display a plurality of selections related to the quality of the radiographic image on a screen for an image quality selection of the user. The user may move a cursor using the mouse or a focus by manipulating an arrow key of the keyboard, and thus may select any one of the plurality of selections. The plurality of selections displayed on the output unit 214 may include at least one of texts and an image. The user may select one quality of the radiographic image or a plurality of qualities of the radiographic images depending on embodiments.

When the first central processing unit 170 or the user determines a quality level of the radiographic image, the tube current obtainer 172 may obtain one or more tube currents with respect to each zone according to the determined quality level. In this case, the tube current obtainer 172 may obtain one or more tube currents for each equivalent object.

Figure 11A:
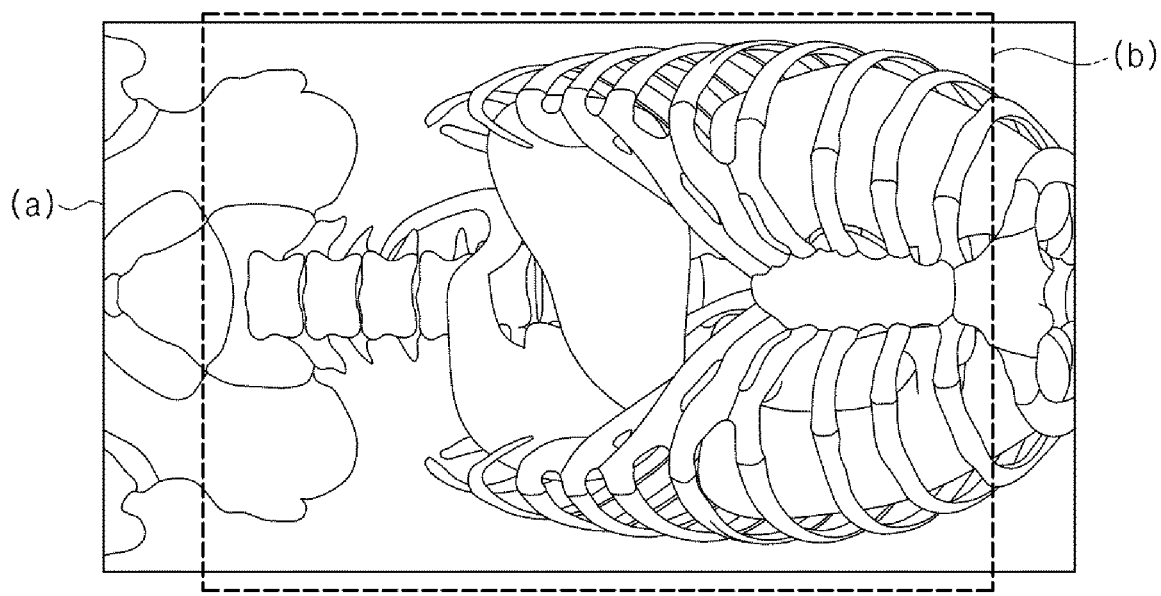
FIGS. 11A, 11B, 12A, and 12B are views for describing a relation between an equivalent object and a tube current, and determination of a tube current in accordance with exemplary embodiments.
Figure 11B:
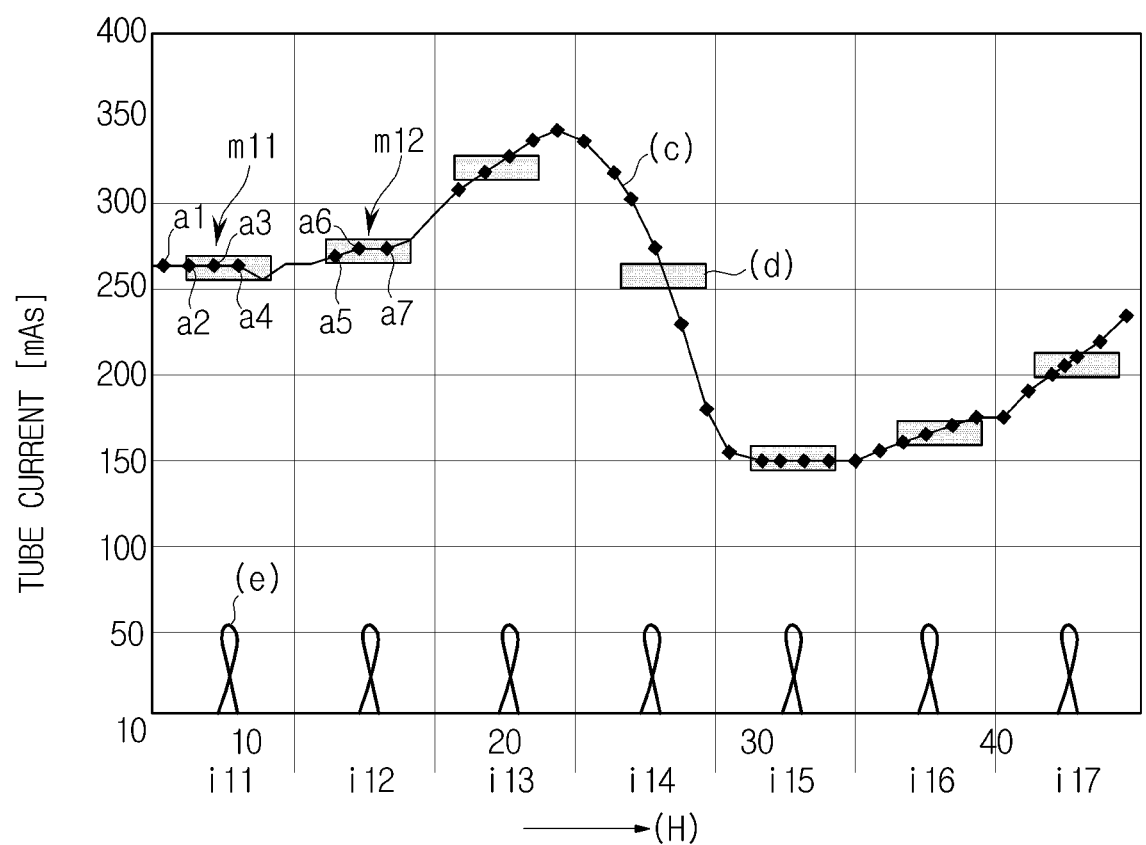
Figure 12A:
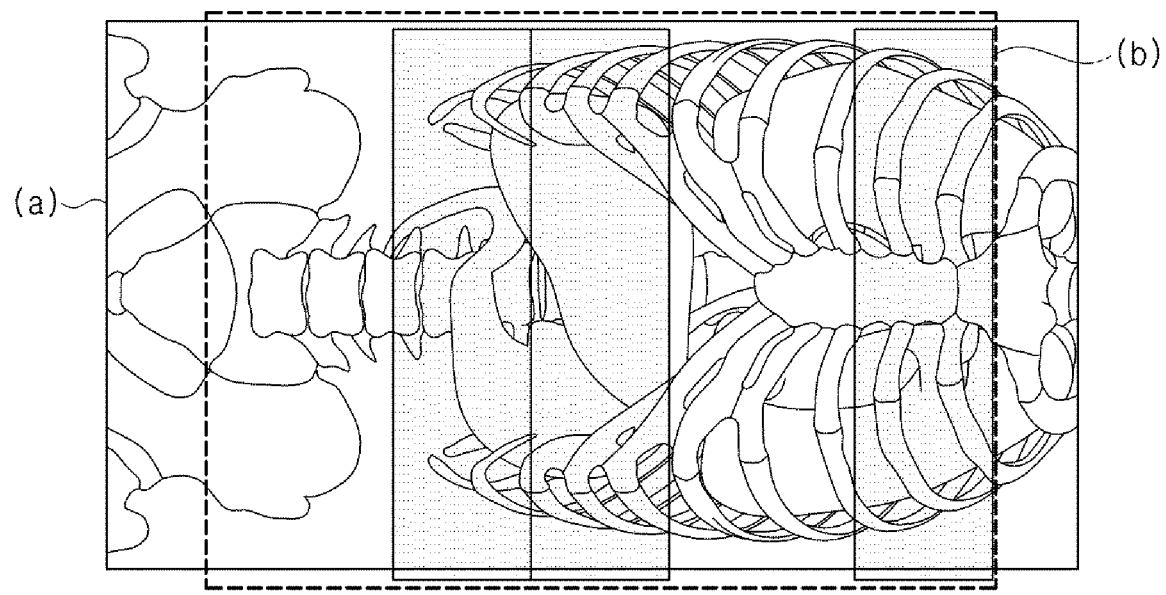
Figure 12B:
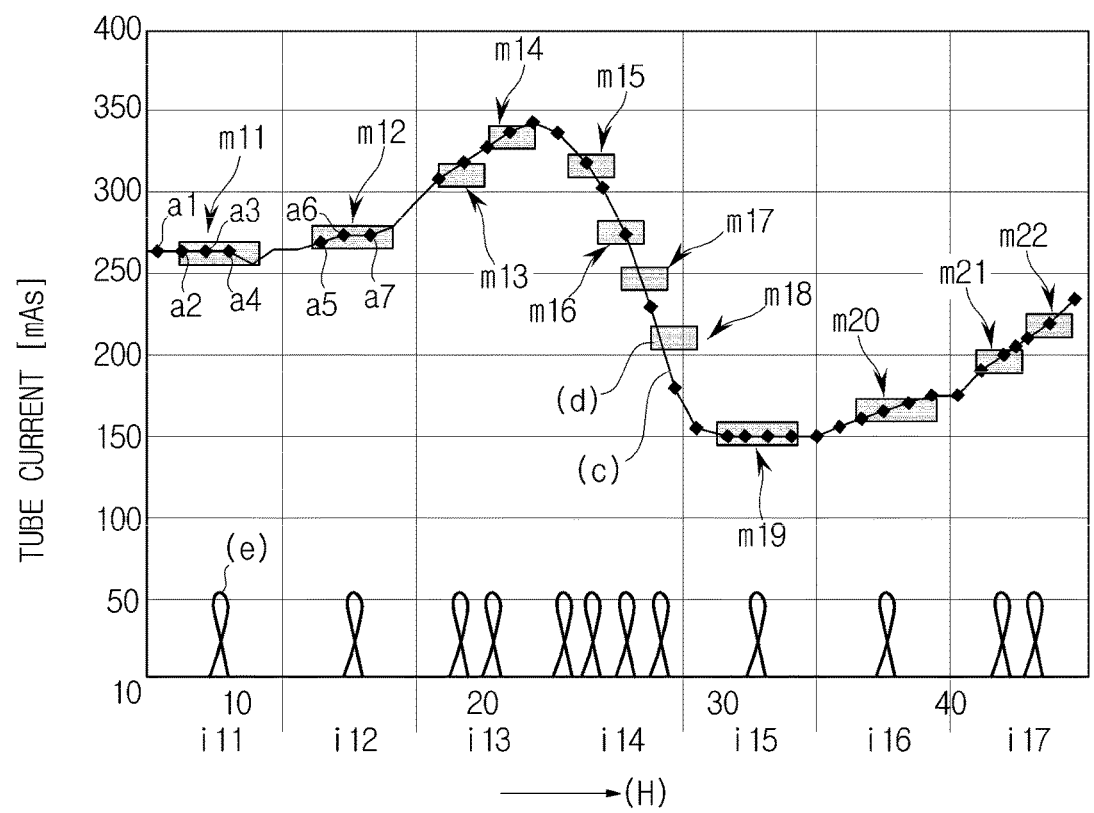

FIGS. 11A, 11B, 12A, and 12B are views for describing a relation between equivalent objects and a tube current, and determination of a tube current in accordance with exemplary embodiments. Y-axes of graphs in FIGS. 11B and 12B represent a tube current, and X-axes thereof represent a position of the object being observed. If the plurality of equivalent objects w11 to w17 as shown in FIG. 10B are determined with respect to a region (b) of interest of a radiographic image (a), obtained by moving the object on the loader 97 at a predetermined speed in the first direction (H) toward the bore 141, as shown in FIG. 11A, a tube current (c), for example, may be obtained as in FIGS. 11B and 12B. The tube current obtainer 172 may obtain one or more tube currents (or tube current levels) (c) for each equivalent object w11 to w17 based on the relation between the equivalent object and the tube current as shown in FIGS. 11B and 12B. In this case, the tube current obtainer 172 may obtain one or more tube currents for each equivalent object w11 to w17. That is, the tube current obtainer 172 may obtain one or more tube currents for each zone i11 to i17. According to an exemplary embodiment, the tube current obtainer 172 may obtain one or more tube currents a1 to a4 corresponding to the equivalent object w11 and one or more tube currents a5 to a7 corresponding to the equivalent object w12. For example, the tube currents a1 to a4, and a5 to a7 may have values proportional to the radiation intensity corresponding to the equivalent object w11 and w12.

According to an exemplary embodiment, when one or one or more tube currents (c) are obtained for each zone i11 to i17 or each equivalent object w11 to w17, the tube current obtainer 172 may calculate an average value (d) of the tube currents for each zone i11 to i17 or each equivalent object w11 to w17. Referring to FIG. 11B, a value m11 is obtained as an average value of the tube currents a1 to a4 corresponding to a first zone i11 or the equivalent object w11, and a value m12 is obtained as an average value of the tube currents a5 to a7 corresponding to a second zone i12 or the equivalent object w12.

The radiation irradiator 110 may irradiate each zone or each equivalent object with the radiation based on the average value (d) of the tube currents (c) corresponding to the each zone or each equivalent object, which is calculated by the tube current obtainer 172. As an example, the radiation irradiator 110 may irradiate each zone or each equivalent object with the radiation to the object based on the average value (d) of the tube currents (c), which is calculated by the tube current obtainer 172, and the gantry 140 may perform one rotation for each zone i11 to i17 or each equivalent object w11 to w17. That is, when the gantry 140 performs one rotation with respect to a certain zone (e.g., i11) or a certain equivalent object (e.g., w11), the radiation irradiator 110 may radiate the radiation based on the average value m11 of the tube currents a1 to a4 corresponding to the zone i11 or the equivalent object w11.

When one or more tube currents (c) with respect to one or more zones i11 to i17 or one or more equivalent objects w11 to w17 of the object are obtained, the parameter determiner 173 may calculate a changed value of attenuation information of the object for each zone to determine whether the changed value is greater than or equal to a threshold value. According to an exemplary embodiment, the attenuation information may be proportional to the tube current (c), and the changed value of the attenuation information may be replaced by the changed value of the tube current (c). Further, since each zone includes one or more equivalent objects, the parameter determiner 173 may calculate a changed value of a width of the equivalent object for each zone to determine whether the changed value of the width of the equivalent object is greater than or equal to the threshold value.

The parameter determiner 173 determines a preset parameter as a parameter for driving the radiographic imaging unit 2, with respect to the zone or the equivalent object in which the changed value is smaller than the threshold value. The preset parameter may include various parameters related to the radiographic imaging apparatus 1, such as an average value (d) of the tube currents (c) for each zone, which is calculated by the tube current obtainer 172, a table feed, a radiation irradiation region, a pitch, the number of rotations (e) per zone of the gantry 140, an image quality level, and the like based on the set quality of the image and the determined equivalent object, and the preset parameter may be values which are input or are previously stored in a manufacturing process or during usage of the CT apparatus 4. As an example, referring to FIGS. 12A and 12B, with respect to the zones i11, i12, i15, and i16 or the equivalent object w11, w12, w15, and w16, in which the changed value is smaller than the threshold value, the preset parameter may be determined as a parameter for driving the radiographic imaging unit 2. For example, as the preset parameters, the tube current may be determined as the average value (d) of the tube currents (c) calculated by the tube current obtainer 172, the pitch may be determined as 1, the radiation irradiation region may be determined as 80 mm, the table feed may be determined as 80 mm/rot, the number of rotations of the gantry 140 may be determined as one rotation per zone.

The parameter determiner 173 may newly obtain the parameter of the zone according to the changed value of the attenuation information or the tube current, with respect to the zone or the equivalent object in which the changed value is greater than or equal to the threshold value. More specifically, referring to FIG. 12B, one or more tube currents of the tube currents (c) corresponding to the attenuation information may be obtained with respect to the zone i13, i14, and i17 or one or more equivalent objects w13, w14, and w17, in which the changed value is greater than or equal to the threshold value, and the tube current (c) may be changed in proportional to the attenuation information. In this case, the parameter determiner 173 may newly obtain the table feed and the radiation irradiation region in the zone i13, i14, and i17 or the equivalent object w13, w14, and w17, and the tube current obtainer 172 may calculate a plurality of tube current average values m13 and m14, m15 to m18, and m19 and m20 respectively with respect to the zone i13, i14, and i17 or the equivalent object w13, w14, and w17. The newly calculated plurality of tube current average values m13 and m14, m15 to m18, and m19 and m20 may be the average values m13 and m14, m15 to m18, and m19 and m20 of the tube current in each sub-zone when the zone or the equivalent object, in which the changed value is greater than or equal to the threshold value, is divided into sub-zones. As an example, the number of the sub-zones may be proportional to a size of the changed value. That is, the sub-zones may be precisely set when the changed value is larger to determine the tube current with respect to each sub-zone.

Specifically, with respect to the zone i13, i14, and i17 or the equivalent object w13, w14, and w17, in which the changed value of the attenuation information or the tube current is greater than or equal to the threshold value, the parameter determiner 173 reduces the table feed, and thus may reduce a movement speed of the loader 97 and may increase the number of rotations per zone of the gantry 140 in the zones i13, i14, and i17 or the equivalent objects w13, w14, and w17.

A relation of the radiation irradiation region (or a range of radiation irradiation) and the table feed may be expressed by the following Equation 2.

Pitch=(a value of the table feed)/(a size of the radiation irradiation region) [Equation 2]

Referring to Equation 2, the parameter determiner 173 may determine the radiation irradiation region, which is irradiated through the first collimator 312 to be proportional to the value of the table feed so that a constant pitch is maintained. The size of the radiation irradiation region may correspond to a size of an opening of the first collimator 130.

On the other hand, the parameter determiner 173 may determine the radiation irradiation region and maintain a constant pitch, and may determine the radiation irradiation region so that the value of the table feed is proportional to the size of the radiation irradiation region.

Since the number of rotations per zone of the gantry 140 is inversely proportional to the table feed, the number of rotations (e) of the gantry 140 in the zones i13, i14, and i17 or the equivalent objects w13, w14, and w17, in which the changed value is greater than or equal to the threshold value, is greater than the number of rotations (d) of the gantry 140 in the zone or the equivalent object, in which the changed value is smaller than the threshold value. For example, the gantry 140 in the zones i11, i12, i15, and i16 or the equivalent objects w11, w12, w15, and w16, in which the changed value is smaller than the threshold value, rotates once with respect to each zone i11, i12, i15, and i16 or each equivalent object w11, w12, w15, and w16, however, the gantry 140 in the zones i13, i14, and i17 or the equivalent objects w13, w14, and w17, in which the changed value is more than the threshold value, rotates once or more times for each sub-zone of the zones i13, i14, and i17.

In this case, the radiation radiated through the radiation irradiator 110 for each rotation (e) or each sub-zone of the zones i13, i14, and i17 may be based on the average value (d) of the tube currents (c) of FIG. 12B obtained by the tube current obtainer 172.

The first central processing unit 170 may perform control to display values of the tube current, the pitch, the table feed, the radiation irradiation region, and the number of rotations per zone of the gantry 140 to the user. For example, the first central processing unit 170 may transfer values of the tube current determined by the tube current obtainer 172, the preset pitch, the table feed determined from the parameter determiner 173 or preset, the radiation irradiation region determined from the parameter determiner 173 or preset, and the preset number of rotations per zone of the gantry 140 to the workstation 200 through the first communicator 192 and the second communicator 211, and the workstation 200 may provide the tube current, the pitch, the table feed, the radiation irradiation region, the number of rotations per zone of the gantry 140 to the user through the output unit 214 such as a display device.

The user may select at least one of values of the tube current, the pitch, the table feed, the radiation irradiation region, and the number of rotations per zone of the gantry 140, which are received through the output unit 214, through the input unit 212 provided in the workstation 200. Alternatively, instead of selecting at least one of values of the tube current, the pitch, the table feed, the radiation irradiation region, and the number of rotations per zone of the gantry 140, the user may input a desired value of at least one of the tube current, the pitch, the table feed, the radiation irradiation region, and the number of rotations per zone of the gantry 140 through the input unit 212. When the user selects at least one of the provided values of the tube current, the pitch, the table feed, the radiation irradiation region, and the number of rotations per zone of the gantry 140 or inputs a desired value of at least one of the tube current, the pitch, the table feed, the radiation irradiation region, and the number of rotations per zone of the gantry 140, the first central processing unit 170 may generate a control command to control the radiation irradiator 110 or the loader 97 according to the selected at least one of values of the tube current, the pitch, the table feed, the radiation irradiation region, and the number of rotations per zone of the gantry 140 or the input desired value of at least one of the tube current, the pitch, the table feed, the radiation irradiation region, and the number of rotations per zone of the gantry 140, and transmit the control command to the radiation irradiator 110, the tube driver 121, the first collimator driver 131, or the transfer device driver 143.

The tube driver 121 may apply the selected value of the tube current or the input desired value of the tube current to the radiation tube 120 of the radiation irradiator 110 according to the control command, and the radiation tube 120 may generate radiation according to the applied tube current and irradiate the object 99 with the radiation. The generated radiation may be absorbed or transmitted through an organ inside the object 99 while passing through the object 99 inside the bore 141. The radiation detector 150 may receive the radiation transmitted through the object 99 and output an electrical signal, and the image processor 191 may generate a radiographic image based on the electrical signal output from the radiation detector 150. The generated radiographic image may be provided to the user through the output unit 214, etc.

Figure 13:
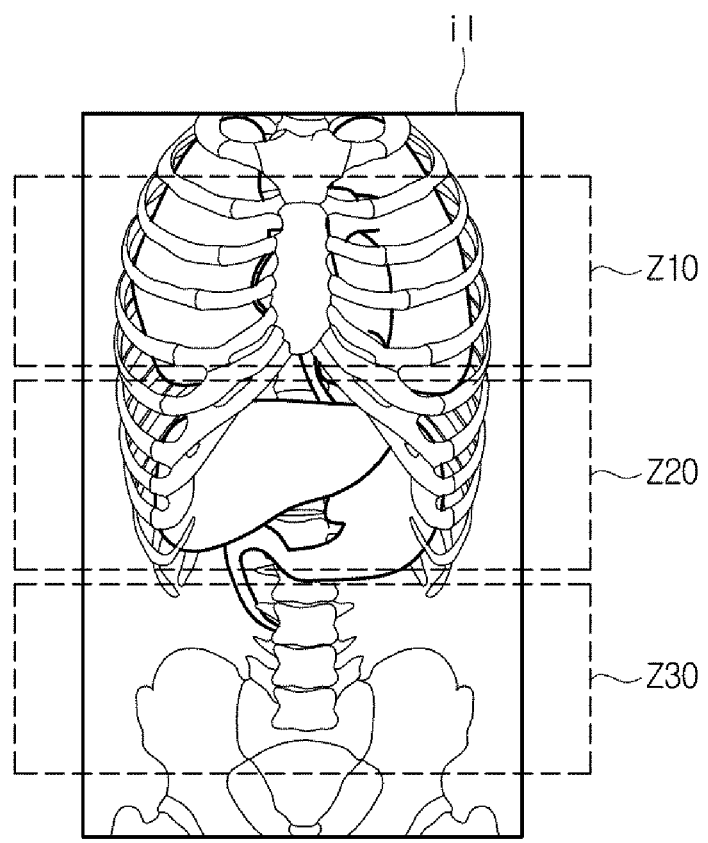
FIG. 13 is a view for describing an example in which a radiographic image is divided into a plurality of zones in accordance with an exemplary embodiment.
Figure 14:
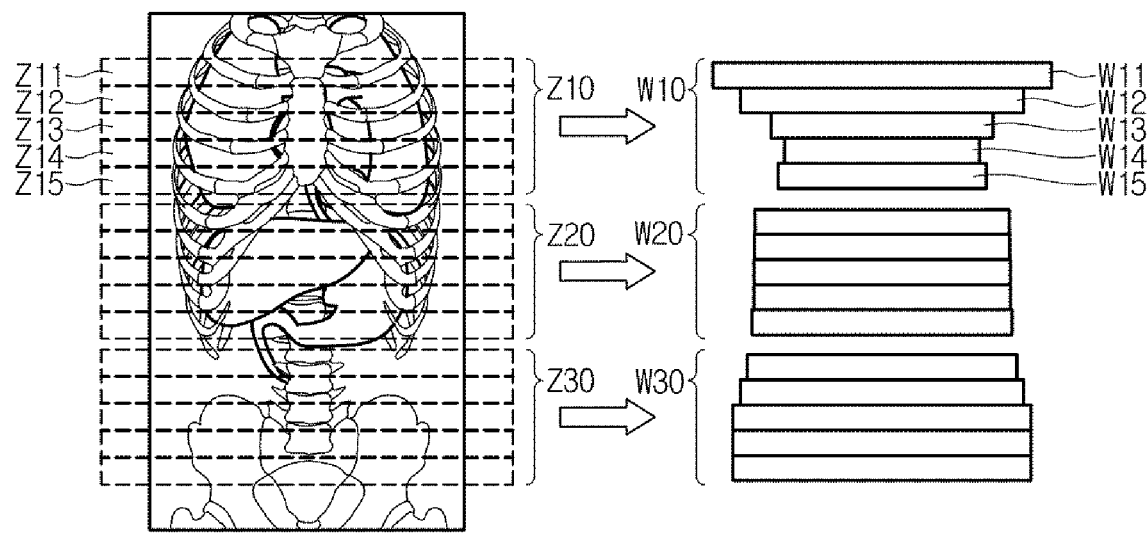
FIG. 14 is a view for describing an example in which an equivalent object is determined for each zone in accordance with an exemplary embodiment.

Hereinafter, an example of performing radiography after a plurality of equivalent objects are determined according to a plurality of zones of a radiographic image will be described with reference to FIGS. 13 and 14. FIG. 13 is a view for describing an example in which a radiographic image is divided into a plurality of zones in accordance with an exemplary embodiment, and FIG. 14 is a view for describing an example in which equivalent objects are determined for each zone in accordance with an exemplary embodiment.

As shown in FIG. 13, a radiographic image i1 may be divided into a plurality of zones, for example, a first zone z10, a second zone z20, and a third zone z30. The division of each zone z10 to z30 may be arbitrarily performed by the first central processing unit 170 or may be performed according to a predefined setting, for example, based on a target region such as an internal organ (e.g., a lung) of the object, and may be performed by the user. In this case, the user may divide the zones z10 to z30 through the input unit 212 of the workstation 200. Here, the zones z10 to z30 may divide only a part of the radiographic image i1, rather than the entire radiographic image i1. The equivalent object determiner 171 may respectively determine equivalent objects w10 to w30 for each zone z10 to z30, as shown in FIG. 14. In other words, the equivalent object determiner 171 may determine a first equivalent object w10 corresponding to the first zone z10, a second equivalent object w20 corresponding to the second zone z20, and a third equivalent object w30 corresponding to the third zone z30. The determination of the equivalent objects w10 to w30 corresponding to the zones z10 to z30 may be performed by using the lookup table 181. The equivalent objects w10 to w30 may be the equivalent objects corresponding to all of the zones z10 to z30. Further, equivalent objects w11 to w15 may be a plurality of equivalent objects obtained by additionally dividing one of the zones, for example, the first zone z10, as shown in FIG. 14. Although not shown in the drawing, a plurality of equivalent objects may be obtained by additionally dividing the zones z20 and z30.

When the equivalent objects are obtained, the tube current obtainer 172 may obtain one or more tube current for each zone using the desired quality of the radiographic image and the equivalent objects. Further, the parameter determiner 173 may determine the parameter for each zone, as shown in FIGS. 11 and 12. Detailed descriptions of the parameter determiner 173 have been provided above and thus will be omitted.

The above-described functions of the first central processing unit 170 and the first storage 180 may be also performed by the second central processing unit 210 and a second storage 213 (see FIG. 4) of the workstation 200.

The first communicator 192 may transmit and receive predetermined data to and from the second communicator 211 of the workstation 200. The first communicator 192 may include at least one of a wired network device such as a local area network (LAN) card, or the like, or a wireless network device such as an antenna, a wireless communication chip, or the like.

The power supply 193 may supply a power source to each component of the CT module 100. The power supply 193 may be implemented by a capacitor which stores electrical energy supplied from a generator provided inside the CT module 100 or from an external commercial power supply.

The CT module 100 may further include an input device such as a keyboard, a mouse, or the like, or an output device such as a display device, a speaker, or the like. The input device or the output device may be installed outside the external housing 98. The user may command to drive the CT module 100 or may input the desired quality of the image using the input device of the CT module 100. Further, the user may obtain information about the selected tube potential and tube current or may receive the image of the object 99 using the output device of the CT module 100.

Hereinafter, the workstation 200 will be described with reference again to FIGS. 2 and 4. Referring to FIGS. 2 and 4, the workstation 200 may receive inputs of various commands from the user, and perform various types of processing according to the input command. Further, the workstation 200 may provide various information such as various processing results or the radiographic image captured by the CT module 100 to the user. The workstation 200 may include the second central processing unit 210, the communicator 211, the input unit 212, the second storage 213, and the output unit 214.

The second central processing unit 210 may perform calculation and processing as needed, and generate a control command to control overall operations of the CT module 100 or the workstation 200. According to an exemplary embodiment, the second central processing unit 210 may perform a function of the first central processing unit 170 of the CT module 100. In this case, the first central processing unit 170 may be omitted. According to another exemplary embodiment, the above-described first central processing unit 170 may perform a function of the second central processing unit 210. The second central processing unit 210 may be implemented using a semiconductor chip, etc.

The second communicator 211 may transmit and receive data to and from the first communicator 192 of the CT module 100. The second communicator 211 may include the wired network device such as an LAN card, or the like, or the wireless network device such as an antenna, a wireless communication chip, or the like. The input unit 212 may receive an input of various information from the user. For example, the input unit 212 may receive, from the user, an input of a setting value for controlling the quality of the radiographic image to be captured. For example, the input unit 212 may include various input device such as a keyboard, a mouse, a keypad, a trackball, a track pad, a touch pad, a touch screen, etc.

The second storage 213 may store various information received from the central processing unit 210. Further, the second storage 213 may also store the lookup table 181. The second central processing unit 210 may read the data from the second storage 213, and may determine the equivalent object, the tube current, and the radiation irradiation region in a manner substantially the same as or similar to the above-described manner using the data read from the second storage 213. In this case, the first storage 180 may be omitted. The second storage 213 may be implemented using at least one of a semiconductor memory device or a magnetic memory device. The output unit 214 may provide various information, for example, the radiographic image or the selected tube potential and tube current to the user. For example, the output unit 214 may include various output devices, such as, a display device, a speaker, a lighting, or the like, capable of displaying or transferring the information to the user.

The above-described workstation 200 may be omitted in the CT apparatus 4 in some exemplary embodiments.

The radiographic imaging apparatus 1 may include a DR apparatus, however, the radiographic imaging apparatus 1 is not limited thereto. For example, the radiographic imaging apparatus may include an FFDM apparatus. The radiographic imaging apparatus 1 may include all of various types of imaging apparatuses which apply a tube potential and/or a tube current to the radiation tube, generate the radiation, and capture the radiographic image.

Figure 15A:
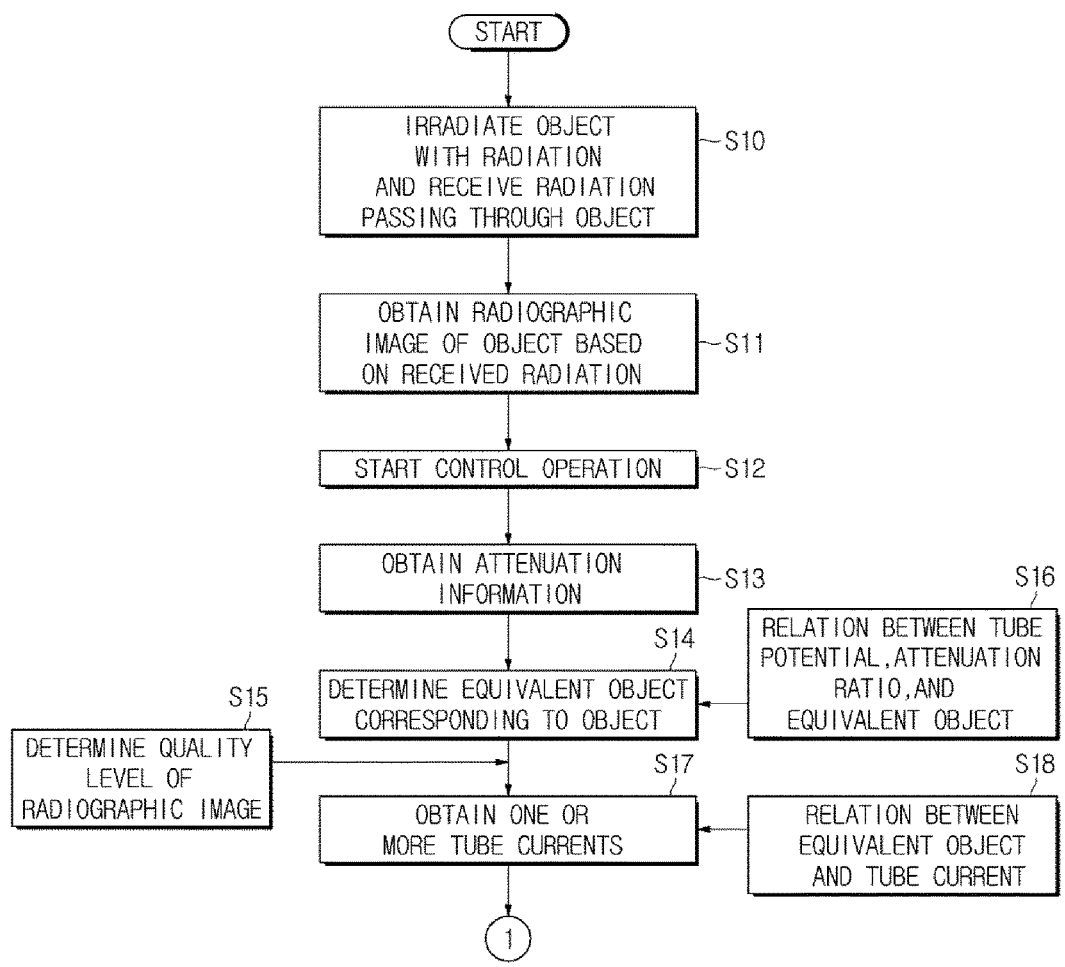
FIGS. 15A, 15B, 15C, 16A, 16B, and 16C are flowcharts of methods of controlling radiographic imaging apparatuses in accordance with exemplary embodiments.
Figure 15B:
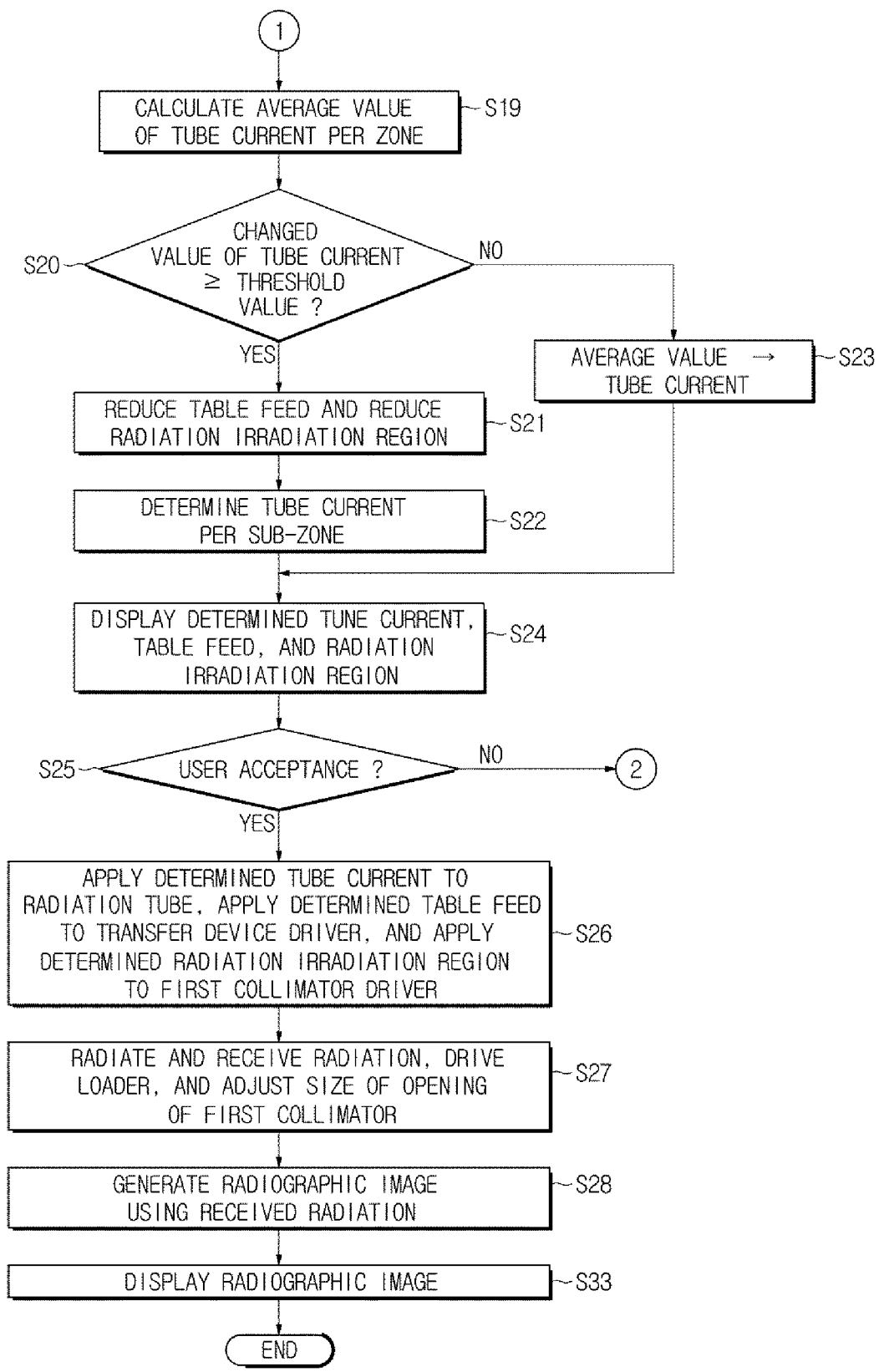
Figure 15C:
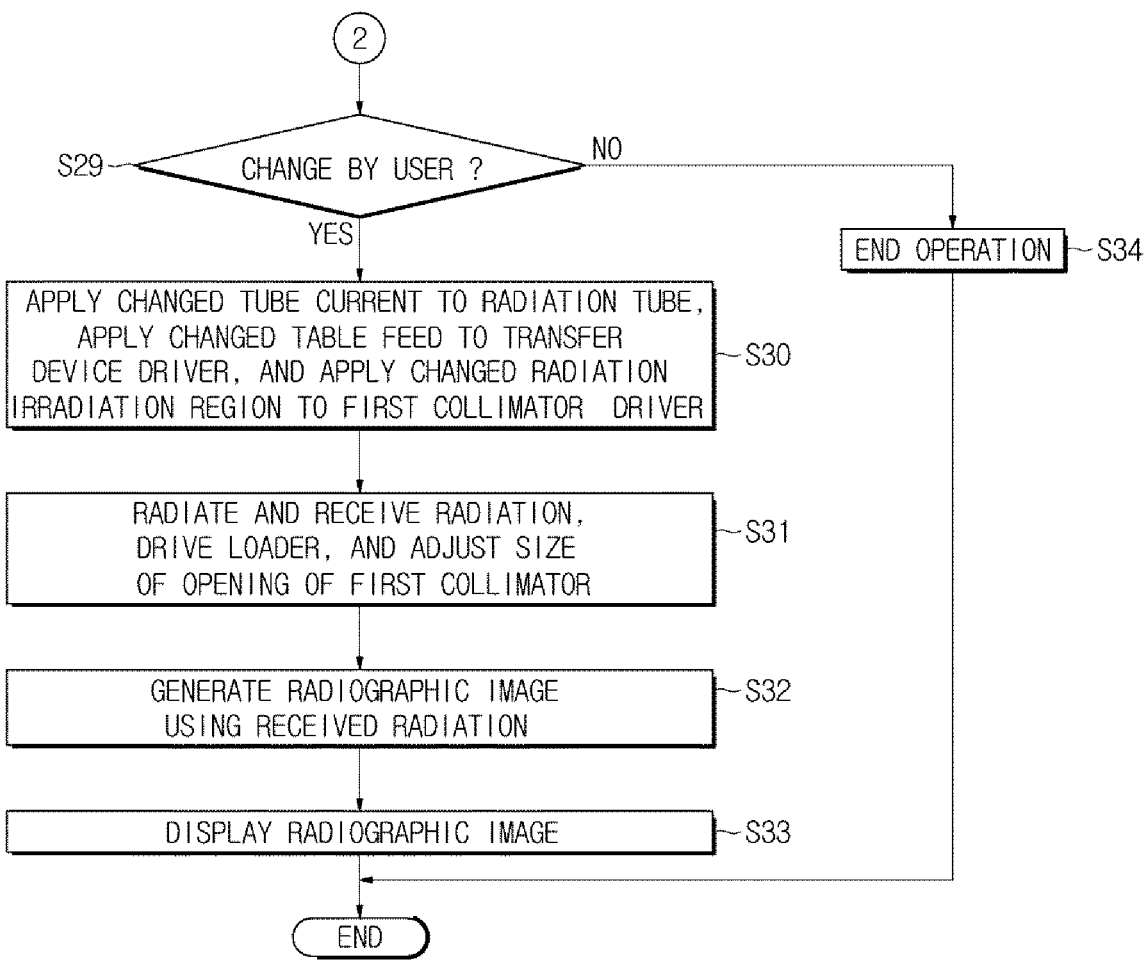

Hereinafter, a method of controlling a radiographic imaging apparatus in accordance with exemplary embodiments will be described with reference to FIGS. 15A to 15C. FIGS. 15A to 15C are flowcharts of a method of controlling a radiographic imaging apparatus in accordance with exemplary embodiments.

As shown in FIGS. 15A to 15C, when a radiation irradiator of a first radiographic imaging apparatus irradiates an object with radiation, the irradiated radiation may pass through the object and reach a radiation detector.

The radiation transmitted through the object may be attenuated according to a characteristic, for example, a density of an internal material of the object. In this case, some of the radiation may not pass through the object and thus may not reach the radiation detector. The radiation detector may receive the radiation transmitted through the object to output an electrical signal (S10). The first radiographic imaging apparatus may obtain a first radiographic image corresponding to the received radiation (S11). Here, the first radiographic imaging apparatus may include a CT apparatus, a DR apparatus, or an FDDM apparatus. In addition, the first radiographic imaging apparatus may include all of various types of imaging apparatuses which apply a tube potential and/or a tube current to a radiation tube, generate the radiation, and capture the radiographic image.

When the first radiographic image is obtained, a second radiographic imaging apparatus starts an operation for performing a method of controlling the second radiography imaging apparatus according to a user's operation or a predefined setting (S12). The second radiographic imaging apparatus may include at least one of a CT apparatus, a DR apparatus, or an FDDM apparatus. In addition, the second radiographic imaging apparatus may include all of various types of imaging apparatuses which apply a tube potential and/or a tube current to a radiation tube, generate the radiation, and capture the radiographic image.

The second radiographic imaging apparatus which performs the method of controlling the second radiographic imaging apparatus and the first radiographic imaging apparatus which captures the radiographic image through the above-described operations S10 and S11 may be the same or different from each other. Further, the second radiographic imaging apparatus and the first radiographic imaging apparatus may be the same type of radiographic imaging apparatuses or different types of radiographic imaging apparatuses. If the second radiographic imaging apparatus, which is different from the first radiographic imaging apparatus used in the above-described operations S10 and S11, is controlled, the first radiographic image obtained in the above-described operations S10 and S11 may be transferred to the second radiographic imaging apparatus by a wired or wireless communication device or by a portable storage device. For example, the first radiographic image obtained by the first radiographic imaging apparatus may be stored in a server connected through a wired and wireless communication network, and the second radiographic imaging apparatus may receive the first radiographic image from the server connected through the wired and wireless communication network.

When the performing of the method of controlling the second radiographic imaging apparatus is started, the second radiographic imaging apparatus obtains attenuation information of the object based on the obtained first radiographic image (S13).

The second radiographic imaging apparatus may determine an equivalent object corresponding to the object based on the first radiographic image (S14). Here, the equivalent object may include a WEO. Specifically, the second radiographic imaging apparatus may determine one or more equivalent objects corresponding to all or a part of the object using the attenuation information with respect to all or the part of the object of the first radiographic image. When the second radiographic imaging apparatus is the same as the first radiographic imaging apparatus, the second radiographic imaging apparatus may determine the equivalent object corresponding to the object based on the electrical signal output from the radiation detector. When a plurality of equivalent objects corresponding to parts of the object are determined, widths of the plurality of corresponding equivalent objects according to characteristics of the parts of the object may be different from each other. Therefore, as shown in FIGS. 10A and 10B, one or more equivalent objects may be determined. One or more zones of the object may be formed based on each equivalent object. That is, one zone may form based on one equivalent object. One or more zones may be units which define a specific part of a human body, for example, a leg, an arm, or an organ, and may be manually set by the user's input or may be automatically recognized and defined by a controller of the second radiographic imaging apparatus based on the electrical signal obtained from the radiographic image or the radiation detector.

According to an exemplary embodiment, the second radiographic imaging apparatus may determine the equivalent object with reference to a lookup table including data with respect to a relation between an attenuation ratio of the object and the equivalent object (S16). The lookup table may be obtained by experimentally measuring the equivalent object corresponding to the object according to the attenuation ratio.

Next, a desired quality of a second radiographic image to be captured by the second radiographic imaging apparatus may be determined (S15). As shown in FIG. 15A, determining a quality level of the second radiographic image may be performed after the method of controlling the second radiographic imaging apparatus is performed. According to another exemplary embodiment, the determining of the quality level of the second radiographic image may be performed before or after the attenuation information of the object is obtained in operation S13. Further, according to another exemplary embodiment, the determining of the quality level of the second radiographic image may be simultaneously performed with the obtaining of the attenuation information of the object in operation S13. Alternatively, the determining of the quality level of the second radiographic image may be performed after the equivalent object is determined in operation S14. The quality of the second radiographic image may be selected or determined by the user using an input device such as a keyboard, a mouse, etc. Further, the quality of the second radiographic image may be selected or determined by a radiography imaging module or the central processing unit of the workstation according to a predefined setting. The quality of the radiographic image may include a noise ratio, a resolution, a contrast ratio, sharpness, etc.

The second radiographic imaging apparatus may obtain one or more tube currents with respect to each equivalent object according to the determined image quality level (S17). The obtaining of one or more tube currents with respect to each equivalent object may include obtaining one or more tube currents for each zone of the object.

The obtaining of one or more tube currents may be performed based on a relation between the equivalent object and the tube current (S18). In an exemplary embodiment, the relation between the equivalent object and the tube current may be experimentally obtained.

The second radiographic imaging apparatus may calculate an average value of the tube currents for each zone or each equivalent object using the obtained one or more tube currents (S19). When the average value of the tube currents for each zone is determined as the tube current applied to the radiation tube by a process described below, the average value of the tube currents may be applied to the radiation tube while the gantry 140 performs a single rotation in each zone.

The second radiographic imaging apparatus determines the zone or the equivalent object, in which changed values of one or more tube currents are greater than or equal to a threshold value (S20). The changed values of one or more tube currents include gradients of one or more tube currents with respect to each zone or each equivalent object according to positions of one or more tube currents of the object. According to another exemplary embodiment, the second radiographic imaging apparatus may determine the zone or the equivalent object, in which a changed value of attenuation information is greater than or equal to a threshold value. The threshold value is a reference for comparison with the changed value of the attenuation information, and the threshold value may be input from the user or previously stored in a manufacturing process or during usage of the second radiographic imaging apparatus.

The second radiographic imaging apparatus reduces the table feed in the corresponding zone and also reduces the size of the radiation irradiation region with respect to the zone in which the changed value of the tube current is determined to be greater than or equal to the threshold value (S21). Further, since the number of rotations per zone of the gantry 140 is increased due to the reduction of the table feed, different tube currents may be obtained each time the gantry 140 rotates, and the tube current with respect to sub-zones of the zone may be determined (S22). The table feed may be inversely proportional to the changed value of the tube current. For example, in the case of a zone corresponding to a lung of the object in which the changed value of the tube current is determined to be greater than or equal to the threshold value, in order to accurately scan the zone, the second radiographic imaging apparatus may reduce the table feed, the gantry 140 rotates several times while performing scanning the lung, and different tube currents may be applied to the radiation tube for each rotation of the gantry 140. In the case in which the same radiation irradiation region is maintained while the table feed is reduced, the radiation dose of the object is increased. In order to prevent this problem, the second radiographic imaging apparatus may also reduce the radiation irradiation region according to reduction of the table feed. On the other hand, the second radiographic imaging apparatus may reduce the table feed after reducing the radiation irradiation region. Therefore, a total radiation exposure dose of the object may be maintained.

The second radiographic imaging apparatus determines the calculated average value of the tube currents as the tube current in the zone in which the changed value is determined as smaller than the threshold value (S23). In the above-described example, the calculated average value of the tube currents is determined as the tube current to be applied to the radiation tube when the gantry 140 rotates once with respect to zones other than a zone corresponding to the lung.

That is, the second radiographic imaging apparatus may accurately scan the zone in which the changed value is determined to be greater than or equal to the threshold value by reducing the table feed and applying the tube current for each individual rotation while reducing the radiation irradiation region to maintain the total radiation dose of the object substantially the same.

The second radiographic imaging apparatus may display the tube current, the table feed, and the radiation irradiation region as the determined parameters to the user through a display device (S24).

The user may determine whether to apply the displayed tube current, the displayed table feed, and the displayed radiation irradiation region to radiographic imaging operation, and may operate an input device such as a keyboard or a mouse to input a result of the determination to the second radiographic imaging apparatus (S25).

When the user determines to apply the displayed tube current to the radiation tube (S26), the second radiographic imaging apparatus may apply the displayed tube current to the radiation tube, and the radiation tube may generate radiation according to the applied tube current. The object is irradiated with the generated radiation, and the radiation detector receives the radiation transmitted through the object (S27). The second radiographic imaging apparatus may generate the second radiographic image using the received radiation (S28). The generated second radiographic image may be displayed to the user through the display device (S33).

Further, when the user determines to apply the displayed table feed and the displayed radiation irradiation region, the second radiographic imaging apparatus may apply the determined table feed to the transfer device driver and apply the determined radiation irradiation region to the first collimator driver (S26). The transfer device driver or the first collimator driver adjusts a movement speed of the loader and a size of an opening of the first collimator according to the applied table feed or radiation irradiation region (S27).

The user may determine not to apply the displayed tube current to the radiation tube and may want to change the tube current (S29). If the user wants to change the tube current, the user may operate the input device to input a desired tube current to be applied to the radiation tube. The second radiographic imaging apparatus may apply the input tube current to the radiation tube (S30), and the radiation tube may generate radiation according to the applied input tube current. The object is irradiated with the generated radiation and the radiation detector may receive the radiation transmitted through the object (S31). The second radiographic imaging apparatus may generate the second radiographic image using the received radiation (S32). The generated second radiographic image may be displayed to the user or the like (S33). When the user determines not to apply the displayed tube current to the radiation tube and does not input a tube current, the second radiographic imaging apparatus may be driven according to a predetermined method. For example, the second radiographic imaging apparatus may perform a process of terminating the radiographic imaging operation (S34).

Further, when the user determines not to apply the displayed table feed or radiation irradiation region, the user may want to change the table feed or the radiation irradiation region (S29). If the user wants to change the table feed or the radiation irradiation region, the user may operate the input device to input a desired table feed or radiation irradiation region to be applied to the transfer device driver or the first collimator driver. The second radiographic imaging apparatus may apply the input parameter to the transfer device driver or the first collimator driver (S30), the transfer device driver may drive the loader according to the applied input table feed, and the first collimator driver may adjust the size of the opening of the first collimator according to the applied input radiation irradiation region. The object may be irradiated with the generated radiation, and the radiation detector may receive the radiation transmitted through the object (S31). The second radiographic imaging apparatus may generate the second radiographic image using the received radiation (S32). The generated second radiographic image may be displayed to the user or the like (S33). When the user determines not to apply the displayed tube current to the radiation tube and does not input a tube current, the second radiographic imaging apparatus may be driven according to a predetermined method. For example, the second radiographic imaging apparatus may perform the process of terminating the radiographic imaging operation (S34).

Figure 16A:
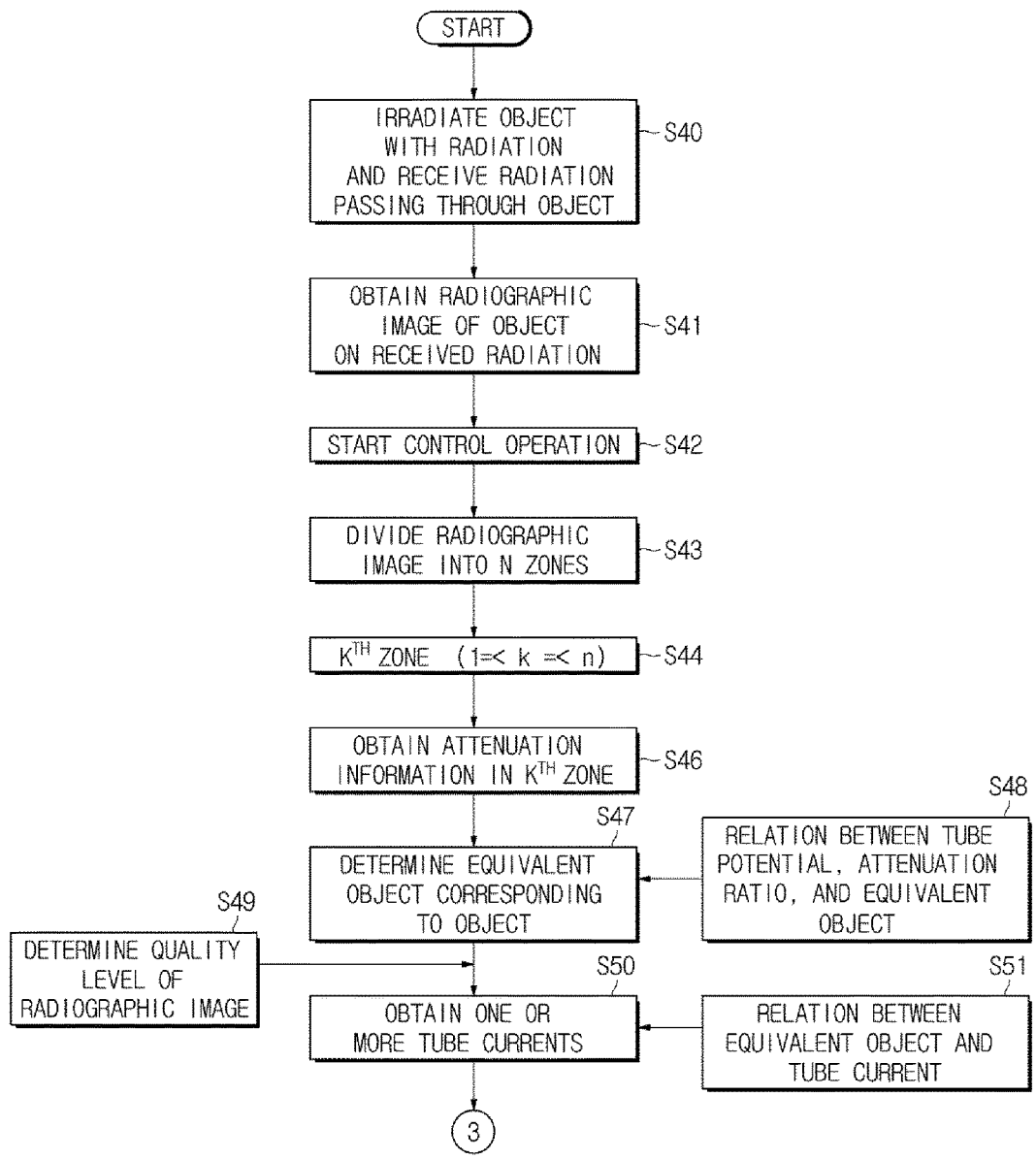
Figure 16B:
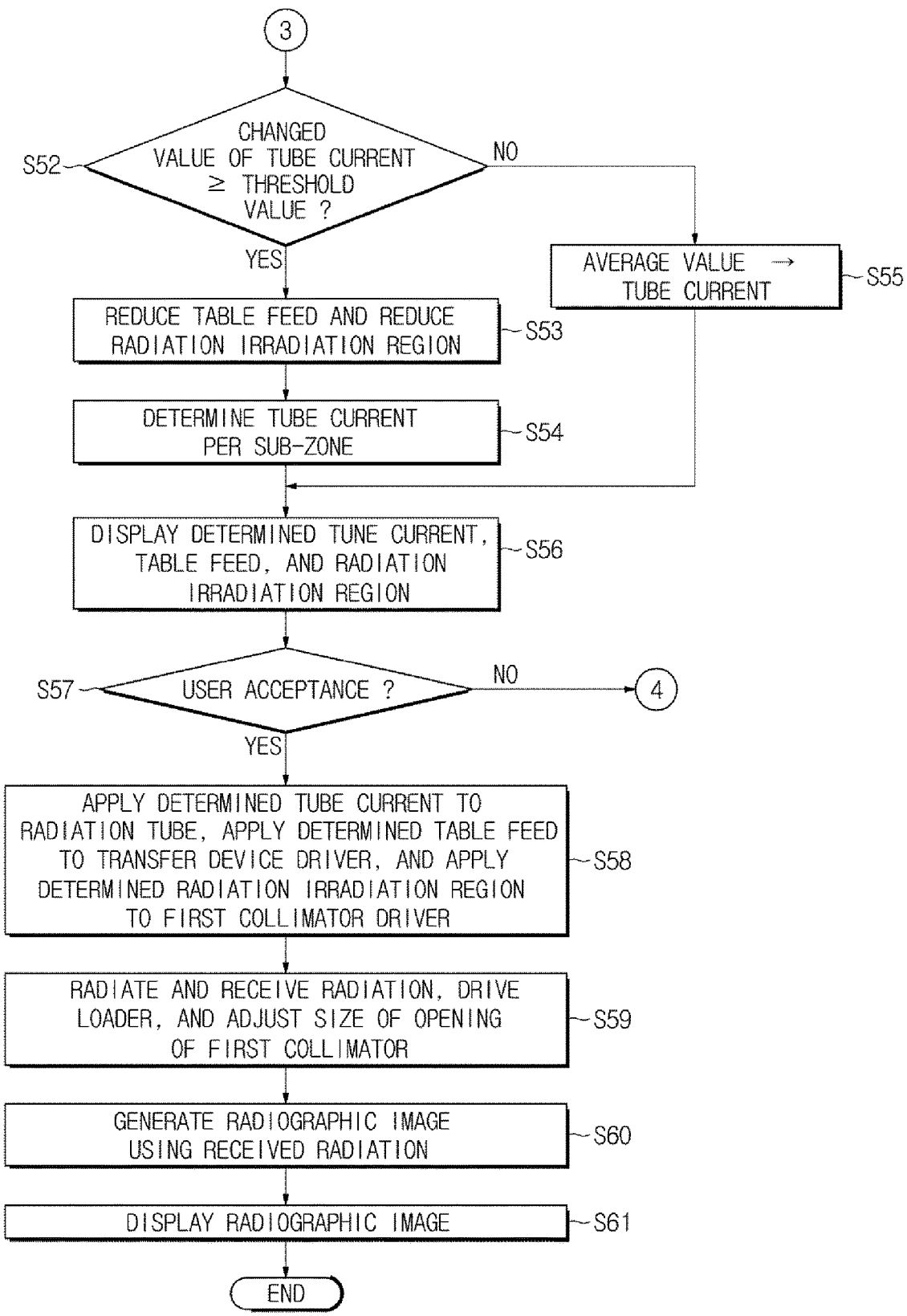
Figure 16C:
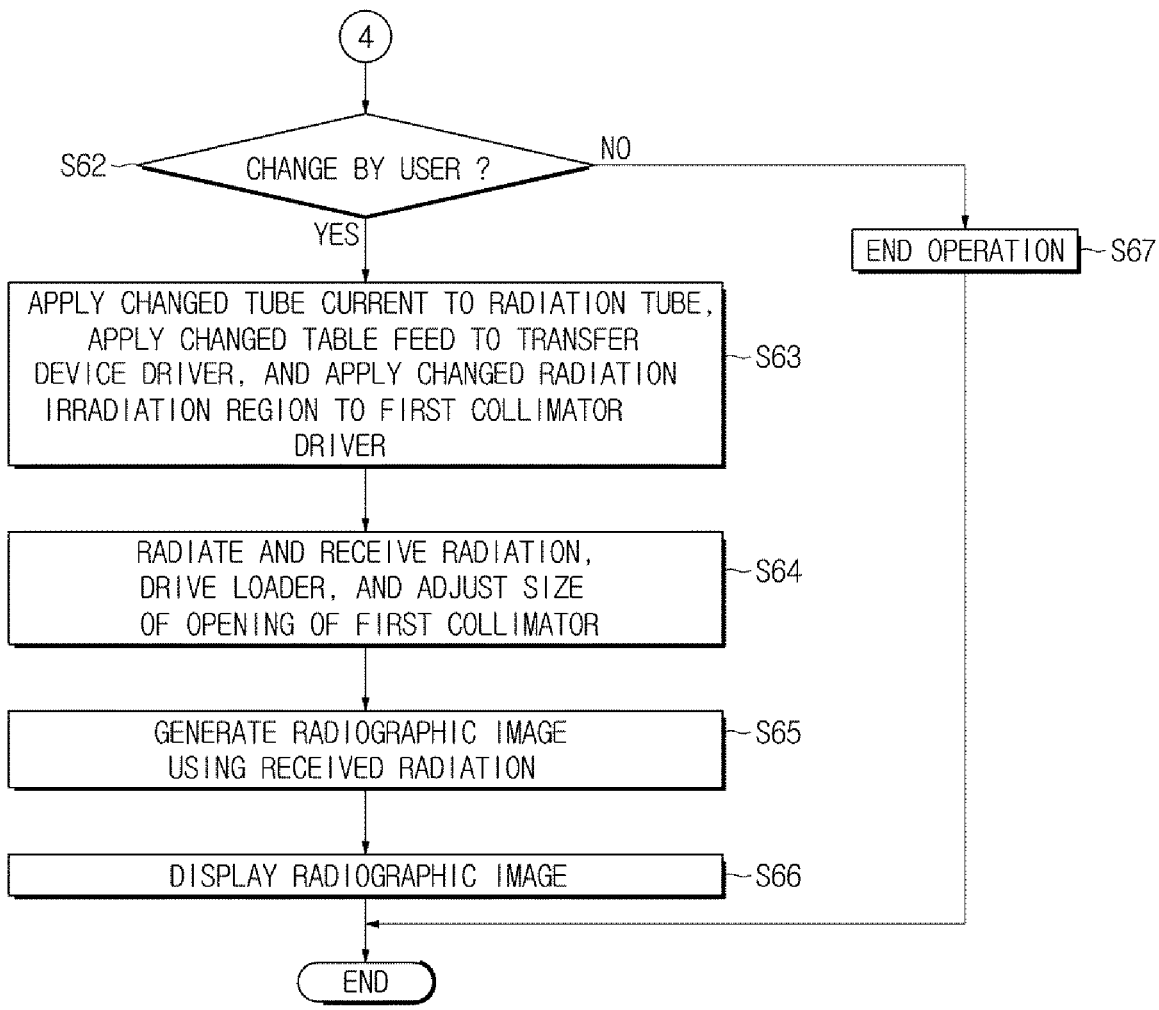

Hereinafter, a method of controlling a radiographic imaging apparatus in accordance with other exemplary embodiments will be described with reference to FIGS. 16A to 16C. FIGS. 16A to 16C are flowcharts of the method of controlling the radiographic imaging apparatus in accordance with other exemplary embodiments.

As shown in FIGS. 16A to 16C, a first radiographic imaging apparatus may irradiate an object with radiation and receive the radiation transmitted through the object (S40), and obtain a first radiographic image with respect to the object (S41).

When the first radiographic image is obtained, a second radiographic imaging apparatus may start an operation for performing the method of controlling the second radiography imaging apparatus according to a user's operation or a predefined setting (S42). Here, the second radiographic imaging apparatus may be the same as or different from the above-described first radiographic imaging apparatus. Further, the second radiographic imaging apparatus may be the same apparatus as or a different apparatus from the first radiographic imaging apparatus. As described in FIGS. 15A to 15C, when the first radiographic imaging apparatus and the second radiographic imaging apparatus are different from each other, the first radiographic image may be transferred to the second radiographic imaging apparatus through a wired or wireless communication device or by a portable storage device. The first radiographic imaging apparatus and the second radiographic imaging apparatus may include all of different types of the radiography imaging apparatuses using a radiation tube as well as the CT apparatus, the DR apparatus, or the FFDM apparatus.

When the method of controlling the second radiographic imaging apparatus is started, the second radiographic imaging apparatus may divide the obtained first radiographic image into a plurality of zones, for example, a first zone to an n-th zone (S43). Here, n denotes a natural number greater than 1.

Then, the second radiographic imaging apparatus may obtain attenuation information of the object in a certain zone, e.g., the first zone (i.e., a k-th zone, wherein k=1) of the first radiographic image (S44 and S46).

The second radiographic imaging apparatus may determine one or more equivalent objects corresponding to the first zone of the object based on the first radiographic image (S47). Here, the equivalent object may include a WEO. When the plurality of corresponding equivalent objects are determined for each part of the first zone, widths of the plurality of corresponding equivalent objects may be different from each other according to a characteristic of each part of the object.

According to an exemplary embodiment, the second radiographic imaging apparatus may determine the equivalent objects with reference to a lookup table which includes data with respect to a relation between an attenuation ratio and the equivalent object (S48). As describe above, the lookup table may be obtained by measuring the equivalent object corresponding to the object according to the attenuation ratio.

The second radiographic imaging apparatus may obtain one or more tube currents when the equivalent object corresponding to the object is determined (S50). To this end, the second radiographic imaging apparatus may first determine a quality of a second radiographic image (S49).

The determination of the quality of the second radiographic image in operation S49 may be performed before or after the attenuation information is obtained in the first zone in operation S46. Alternatively, the determination of the quality of the second radiographic image may be simultaneously performed with the obtaining of the attenuation information in the first zone. Still alternatively, the determination of the quality of the second radiographic image may be performed after the determination of the equivalent object in operation S47. The user may operate an input device to input a quality of the second radiographic image, and thus the quality of the second radiographic image may be determined based on a user input (S49). Further, the radiography imaging module or the central processing unit of a workstation may determine the quality of the second radiographic image according to a predetermined setting. The quality of the second radiographic image may include a noise ratio, a resolution, a contrast ratio, sharpness, or the like.

The obtaining of one or more tube currents (S50) may be performed based on the relation between the equivalent object and the tube current (S51). In an exemplary embodiment, and the relation between the equivalent object and the tube current may be experimentally obtained.

The second radiographic imaging apparatus may calculate an average value of the tube currents in the first zone using the obtained one or more tube currents. When the average value of the tube currents with respect to the first zone is determined as the tube current to be applied to the radiation tube (S55) by a process described below, the average value of the tube current may be applied to the radiation tube while a gantry 140 performs a single rotation in the first zone.

The second radiographic imaging apparatus determines whether a changed value of one or more tube currents in the first zone is greater than or equal to a threshold value (S52). The changes values of one or more tube currents include a gradient of one or more tube currents according to a position of the object with respect to each zone. According to another exemplary embodiment, the second radiographic imaging apparatus may determine whether a changed value of attenuation information is greater than or equal to a threshold value. The threshold value is a reference value for comparison with the changed value of the attenuation information, and the threshold value may be input from the user or previously stored in a manufacturing process or during usage of the second radiographic imaging apparatus.

When it is determined that the changed values of one or more tube currents in the first zone are greater than or equal to the threshold value, the second radiographic imaging apparatus reduces a table feed in the first zone and also reduces the size of a radiation irradiation region (S53).

Further, since the number of rotations per zone of the gantry 140 is increased due to the reduction of the table feed, different tube currents may be obtained each time the gantry 140 rotates, and tube current with respect to sub-zones of the first zone may be determined (S54). The table feed may be inversely proportional to the changed value of one or more tube currents. For example, in the case in which the first zone is a zone corresponding to a lung of the object in which the changed value of one or more tube currents is determined to be greater than or equal to the threshold value, in order to accurately scan the zone, the second radiographic imaging apparatus may reduce the table feed, the gantry 140 rotates several times while performing scanning the lung, and different tube currents may be applied to the radiation tube for each rotation of the gantry 140. In the case in which the same radiation irradiation region is maintained while the table feed is reduced, the radiation dose of the object is increased. In order to prevent this problem, the second radiographic imaging apparatus may also reduce the radiation irradiation region according to reduction of the table feed. On the other hand, the second radiographic imaging apparatus may reduce the table feed after reducing the radiation irradiation region. Therefore, a total exposure dose of the object may be maintained substantially the same as when the average value of the tube currents is applied to the zone.

When it is determined that the changed value is smaller than the threshold value, the second radiographic imaging apparatus determines the calculated average value of the tube currents as the tube current of the first zone (S55). According to the above-described example, when the first zone is not a zone corresponding to the lung, the calculated average value of the tube currents may be determined as the tube current applied to the radiation tube when the gantry 140 rotates once.

That is, when the changed value of the zone is greater than or equal to the threshold value, the second radiographic imaging apparatus may accurately scan the zone by reducing the table feed and applying the tube current for each individual rotation while maintaining the total radiation exposure dose of the object by reducing the radiation irradiation region.

The second radiographic imaging apparatus may obtain attenuation information of the object (S46), determine one or more equivalent objects (S47 to S48), and obtain one or more tube currents (S49 to S50) with respect to a second zone (i.e., a k-th zone, wherein k=2) similar to the above-described process performed with respect to the first zone. Further, the second radiographic imaging apparatus may determine a parameter for the second zone according to the changed value of the tube current (S52 to S55).

The second radiographic imaging apparatus may perform the processes (S46 to S55) up to an n-th zone, and may display the tube current, the table feed, and the radiation irradiation region as the determined parameters to the user through the display device (S56).

The user may determine to apply the displayed tube current, table feed, and radiation irradiation region to the radiographic imaging operation, and may operate an input device such as a keyboard or a mouse to input to the second radiographic imaging apparatus (S57).

When the user determines to apply the displayed tube current to the radiation tube (S58), the second radiographic imaging apparatus may apply the displayed tube current to the radiation tube, and the radiation tube may generate radiation according to the applied tube current. The object is irradiated with the generated radiation, and the radiation detector receives the radiation transmitted through the object (S59). The second radiographic imaging apparatus may generate the second radiographic image using the received radiation (S60). The generated second radiographic image may be displayed to the user through the display device (S61).

Further, when the user determines to apply the displayed table feed and radiation irradiation region (S58), the second radiographic imaging apparatus may apply the determined table feed to the transfer device driver and the determined radiation irradiation region to the first collimator driver. The transfer device driver or the first collimator driver adjusts a movement speed of the loader and a size of an opening of the first collimator according to the applied table feed or radiation irradiation region (S59).

The user may determine not to apply the displayed tube current to the radiation tube and may want to change the tube current (S62). If the user wants to change the tube potential and the tube current, the user may operate the input device to input a desired tube current to be applied to the radiation tube. The second radiographic imaging apparatus may apply the input tube current to the radiation tube (S63), and the radiation tube may generate the radiation according to the applied tube current. The object is irradiated with the generated radiation and the radiation detector may receive the radiation transmitted through the object (S64). The second radiographic imaging apparatus may generate the second radiographic image using the received radiation (S65). The generated second radiographic image may be displayed to the user or the like (S66). When the user determines not to apply the displayed tube current to the radiation tube and does not input a new tube current, the second radiographic imaging apparatus may be driven according to a predetermined method. For example, the second radiographic imaging apparatus may perform a process of terminating the radiographic imaging operation (S67).

Further, when the user does not determine to apply the displayed table feed or radiation irradiation region, the user may want to change the table feed or the radiation irradiation region (S62). If the user wants to change the table feed or the radiation irradiation region, the user may operate the input device to input a desired table feed or radiation irradiation region to be applied to the transfer device driver or the first collimator driver. The second radiographic imaging apparatus may apply the changed parameter to the transfer device driver or the first collimator driver (S63), the transfer device driver may drive the loader according to the applied table feed, and the first collimator driver may adjust the size of the opening of the first collimator according to the applied radiation irradiation region. The object may be irradiated with the generated radiation, and the radiation detector may receive the radiation transmitted through the object (S64). The second radiographic imaging apparatus may generate the second radiographic image using the received radiation (S65). The generated second radiographic image may be displayed to the user or the like (S66). When the user determines not to apply the displayed table feed or radiation irradiation region and does not input a new table feed or radiation irradiation region, the second radiographic imaging apparatus may be driven according to a predetermined method. For example, the second radiographic imaging apparatus may perform a process of terminating the radiographic imaging operation (S67).

According to the radiographic imaging apparatus and the method of controlling the same according to exemplary embodiments, a radiographic image which is desired by a user may be obtained according to a zone of an object while a radiation exposure dose of the object is minimized, and thus the object such as a human body or the like may be prevented from being exposed to a large amount of radiation.

According to the radiographic imaging apparatus and the method of controlling the same according to exemplary embodiments, an appropriate parameter capable of obtaining higher image quality may be determined while a radiation exposure dose of an object is minimized.

According to the radiographic imaging apparatus and the method of controlling the same according to exemplary embodiments, an optimal parameter capable of obtaining a radiographic image which is easily read by a user may be determined while a total radiation exposure dose is maintained.

According to the radiographic imaging apparatus and the method of controlling the same according to exemplary embodiments, since an optimal parameter may be determined even though information about a size or a characteristic of an object is not input by an operator of the apparatus, convenience of a user who uses the radiographic imaging apparatus may be improved.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A radiographic imaging apparatus, comprising:
a radiation irradiator configured to irradiate radiation to an object;
a radiation detector configured to detect an intensity of the radiation passing through the object;
a loader configured to load the object;
a controller configured to divide the object into one or more zones based on the intensity of the radiation, and wherein the controller is further configured to change at least one of a movement speed of the loader and a range of radiation irradiation of the radiation irradiator according to a change in the intensity of the radiation with respect to a zone of the object, when the change in the intensity of the radiation in the zone is greater than or equal to a threshold value.

2. The apparatus according to claim 1, wherein the controller is further configured to obtain a current tube current with respect to the one or more zones of the object, based on the intensity of the radiation in the one or more zones of the object.

3. The apparatus according to claim 2, wherein:
the controller is further configured to determine a next tube current of a zone, in which the change in the intensity of the radiation is greater than or equal to the threshold value, according to the change in the intensity of the radiation; and
the radiation irradiator is further configured to irradiate the radiation to the object corresponding to the next tube current of the zone.

4. The apparatus according to claim 2, wherein the controller determines one or more equivalent objects corresponding to the one or more zones of the object based on the intensity of the radiation passing through the object, a width of the one or more zones being determined based on a width of a corresponding equivalent object.

5. The apparatus according to claim 2, wherein the controller is further configured to obtain an average value of the current tube current obtained with respect to one or more zones, and the controller is further configured to determine a next tube current of a zone based on the average value of the current tube current when the change in the intensity of the radiation is smaller than the threshold value.

6. The apparatus according to claim 1, wherein the controller changes at least one of the movement speed of the loader and the range of the radiation irradiation while maintaining a substantially constant ratio of a value of the movement speed of the loader to a value of the range of the radiation irradiation.

7. The apparatus according to claim 1, wherein the controller is further configured to determine a next tube current with respect to one or more zones of the object, wherein:
the radiation irradiator is further configured to irradiate the radiation to a zone of the object according to a next tube current determined with respect to the zone; and
the controller is further configured to maintain a total amount of the next tube current with respect to the one or more zones to be substantially constant.

8. The apparatus according to claim 1, wherein the controller changes the movement speed of the loader inversely proportional to the change in the intensity of the radiation, when the change in the intensity of the radiation is greater than or equal to the threshold value.

9. The apparatus according to claim 1, wherein the controller changes the range of the radiation irradiation of the radiation irradiator inversely proportional to the change in the intensity of the radiation, when the change in the intensity of the radiation is greater than or equal to the threshold value.

10. The apparatus according to claim 1, wherein the controller changes a number of rotations of the radiation irradiator according to the change in the intensity of the radiation, when the change in the intensity of the radiation is greater than or equal to the threshold value.

11. The apparatus according to claim 1, wherein the controller is further configured to obtain one or more zones of the object by dividing the object based on the intensity of the radiation.

12. The apparatus according to claim 1, further comprising an input unit configured to receive, from a user, an input of at least one of an image quality, the range of the radiation irradiation, the movement speed of the loader, and a pitch.

13. A method of controlling a radiographic imaging apparatus, the method comprising:
irradiating radiation to an object;
detecting an intensity of the radiation passing through the object;
dividing the object into one or more zones based on the intensity of the radiation; and
controlling at least one of a movement speed of a loader configured to load the object and a range of radiation irradiation according to a change in the intensity of the radiation with respect to a zone of the object, when the change in the intensity of the radiation in the zone is greater than or equal to a zone threshold value.

14. The method according to claim 13, further comprising:
obtaining a current tube current with respect to one or more zones of the object based on the intensity of the radiation; and
determining a next tube current of a zone, in which the change in the intensity of the radiation is greater than or equal to the threshold value, according to the change in the intensity of the radiation.

15. The method according to claim 13, wherein the controlling further comprises controlling at least one of the movement speed of the loader configured to load the object and the range of the radiation irradiation according to the change in the intensity of the radiation, while maintaining a substantially constant ratio of a value of the movement speed of the loader to a value of the range of the radiation irradiation.

16. The method according to claim 13, further comprising obtaining a current tube current of each zone of the object based on an average value of the intensity of the radiation in the each zone of the object.

17. The method according to claim 13, wherein the controlling further comprises performing control such that the movement speed of the loader is changed inversely proportional to the change in the intensity of the radiation with respect to a zone of the object, when the change in the intensity of the radiation in the zone is greater than or equal to the threshold value.

18. The method according to claim 13, wherein the controlling comprises performing control such that the range of the radiation irradiation is changed inversely proportional to the change in the intensity of the radiation with respect to a zone of the object, when the change in the intensity of the radiation in the zone is greater than or equal to the threshold value.

19. A radiographic imaging apparatus, comprising:
a radiographic imaging unit configured to obtain a radiographic image with respect to an object; and
a processor configured to obtain attenuation information of the object based on the radiographic image and obtain one or more zones of the object by dividing the object based on the attenuation information,
wherein the processor is configured to change at least one of a plurality of parameters for driving the radiographic imaging unit with respect to a zone of the object based on a change in the attenuation information in a corresponding zone,
wherein the processor is further configured to:
obtain a current tube current with respect to the one or more zones based on the attenuation information,
when the change in the attenuation information in a first zone of the object is smaller than a threshold, determine a next tube current based on an average value of a current tube current with respect to the first zone of the object, and
control the radiographic imaging unit to obtain a second radiographic image with respect to the first zone of the object using the next tube current.

20. The radiographic imaging apparatus of claim 19, wherein the parameters comprise at least one of tube currents with respect to one or more zones, a movement speed of a loader configured to load the object, a range of radiation irradiation, a pitch, a number of rotations of a gantry, and an image quality level, the image quality level comprising at least one of a noise ratio, a resolution, a contrast ratio, and a sharpness.

21. The radiographic imaging apparatus of claim 20, wherein the processor is further configured to reduce at least one of the movement speed of the loader and the range of the radiation irradiation with respect to a certain zone of the object, when the change in the attenuation information in the certain zone is greater than or equal to a threshold value.

22. The radiographic imaging apparatus of claim 19, wherein the processor is further configured to:
obtain a current tube current with respect to the one or more zones based on the attenuation information,
when the change in the attenuation information in a second zone is equal to or greater than a threshold, divide the second zone into a plurality of sub-zones and determine a plurality of next tube currents for the plurality of sub-zones, respectively, based on an average value of the current tube current with respect to each sub-zone of the object, and
control the radiographic imaging unit to obtain a second radiographic image with respect to the second zone of the object by using the plurality of next tube currents.

23. The radiographic imaging apparatus of claim 22, wherein a number of the plurality of sub-zones obtained by dividing the second zone is proportional to a size of the change in the attenuation information in the second zone.

24. The radiographic imaging apparatus of claim 19, wherein the processor is further configured to obtain the one or more zones of the object by using a lookup table, the lookup table comprising data indicating a relationship between a width of an equivalent object and the attenuation information, a width of the one or more zones being determined based on a width of a corresponding equivalent object.

* * * * *